(12) United States Patent
Sabata

(10) Patent No.: US 11,439,366 B2
(45) Date of Patent: Sep. 13, 2022

(54) IMAGE PROCESSING APPARATUS, ULTRASOUND DIAGNOSIS SYSTEM, OPERATION METHOD OF IMAGE PROCESSING APPARATUS, AND COMPUTER-READABLE RECORDING MEDIUM

(71) Applicant: OLYMPUS CORPORATION, Tokyo (JP)

(72) Inventor: Tomohiro Sabata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 654 days.

(21) Appl. No.: 16/441,147

(22) Filed: Jun. 14, 2019

(65) Prior Publication Data

US 2019/0357887 A1 Nov. 28, 2019

Related U.S. Application Data

(63) Continuation of application No. PCT/JP2017/044440, filed on Dec. 11, 2017.

(30) Foreign Application Priority Data

Dec. 19, 2016 (JP) .............................. JP2016-245747

(51) Int. Cl.
*A61B 8/00* (2006.01)
*G09G 5/08* (2006.01)
(Continued)

(52) U.S. Cl.
CPC .............. *A61B 8/469* (2013.01); *A61B 8/461* (2013.01); *A61B 8/465* (2013.01); *A61B 8/467* (2013.01);
(Continued)

(58) Field of Classification Search
CPC ......... A61B 8/469; A61B 8/461; A61B 8/465; A61B 8/467; A61B 8/12; A61B 8/06;
(Continued)

(56) References Cited

U.S. PATENT DOCUMENTS 6,259,436 B1 * 7/2001 Moon ................... G06F 3/0488
715/810
2010/0179427 A1 * 7/2010 Yamamoto ............. A61B 8/469
600/443
(Continued)

FOREIGN PATENT DOCUMENTS

JP   H06-292666 A   10/1994
JP   2011-255082 A  12/2011
JP   2014-128318 A   7/2014

OTHER PUBLICATIONS

International Search Report dated Jan. 16, 2018 issued in PCT/JP2017/044440.

*Primary Examiner* — Sean D Mattson
(74) *Attorney, Agent, or Firm* — Scully, Scott, Murphy & Presser, P.C.

(57) ABSTRACT

An image processing apparatus includes: a display controller configured to cause a display to display an image including a first pointer having a predetermined shape superimposed thereon and move a position of the first pointer within the image in accordance with an input position that is input from an input device; a region-of-interest setting circuit configured to set a region corresponding to the position of the first pointer within the image as a region of interest when a confirmation operation for confirming the input position is input to the input device; and a distance determining circuit configured to determine a distance between a first representative position of the first pointer and a second representative position of the region of interest within the image.

10 Claims, 26 Drawing Sheets

(51) Int. Cl.
*G01S 7/52* (2006.01)
*A61B 8/12* (2006.01)

(52) U.S. Cl.
CPC ...... *G01S 7/52071* (2013.01); *G01S 7/52073* (2013.01); *G09G 5/08* (2013.01); *A61B 8/12* (2013.01); *G06T 2207/20104* (2013.01); *G09G 2340/0464* (2013.01); *G09G 2340/12* (2013.01); *G09G 2354/00* (2013.01); *G09G 2380/08* (2013.01)

(58) Field of Classification Search
CPC ......... A61B 8/48; A61B 8/5223; A61B 1/045; G01S 7/52071; G01S 7/52073; G06T 2207/20104; G06T 1/00; G09G 5/08; G09G 2340/0464; G09G 2340/12; G09G 2354/00; G09G 2380/08; G06F 3/147; G16H 50/30

See application file for complete search history.

(56) References Cited

U.S. PATENT DOCUMENTS

| | | | |
|---|---|---|---|
| 2013/0324850 A1* | 12/2013 | Petruzzelli | A61B 8/465 600/407 |
| 2014/0187936 A1 | 7/2014 | Nakamura et al. | |
| 2014/0258941 A1* | 9/2014 | Lim | G06T 7/13 715/862 |
| 2015/0289844 A1* | 10/2015 | Okamoto | A61B 8/469 600/443 |
| 2016/0361044 A1* | 12/2016 | Hibi | A61B 8/54 |
| 2017/0090675 A1* | 3/2017 | Lee | A61B 8/469 |

\* cited by examiner

IMAGE PROCESSING APPARATUS, ULTRASOUND DIAGNOSIS SYSTEM, OPERATION METHOD OF IMAGE PROCESSING APPARATUS, AND COMPUTER-READABLE RECORDING MEDIUM

CROSS-REFERENCE TO RELATED APPLICATION

This application is a continuation of PCT International application Ser. No. PCT/JP2017/044440, filed on Dec. 11, 2017 which designates the United States, incorporated herein by reference, and which claims the benefit of priority from Japanese Patent Applications No. 2016-245747, filed on Dec. 19, 2016, incorporated herein by reference.

BACKGROUND

The present disclosure relates to an image processing apparatus, an ultrasound diagnosis system, an operation method of the image processing apparatus, and a computer-readable recording medium.

Ultrasound elastography is conventionally known as a technology for diagnosing an observation target by using ultrasound waves. The ultrasound elastography is a technology using differences in the rigidity of a tumor or tumor tissue in a living body depending on the disease progress status or the living body. In this technology, an elasticity image, which is an image of information about the rigidity of living tissue, is generated by adding color with the average value of the amount of displacement of the living tissue in the set region of interest (ROI) as the reference value.

During ultrasound elastography, the operator sets the region of interest in accordance with observation details. Furthermore, during ultrasound elastography, in some cases, the operator sets multiple regions of interest and compares the rigidity with respect to each region of interest (see, for example, Japanese Laid-open Patent Publication No. 2011-255082).

SUMMARY

An image processing apparatus according to the disclosure includes: a display controller configured to cause a display to display an image having a first pointer superimposed thereon and move a position of the first pointer within the image in accordance with an input position that is input from an input device, the first pointer having a predetermined shape; a region-of-interest setting circuit configured to set a region corresponding to the position of the first pointer within the image as a region of interest when a confirmation operation for confirming the input position is input to the input device; and a distance determining circuit configured to determine a distance between a first representative position of the first pointer and a second representative position of the region of interest within the image. The distance determining circuit is configured to determine whether the confirmation operation has been performed and, when the confirmation operation has not been performed, processing is terminated or, when the confirmation operation has been performed and when the distance determining circuit determines that the distance between the first representative position and the second representative position is shorter than a predetermined distance, the display controller switches the region of interest to an editable state.

An ultrasound diagnosis system according to the disclosure includes: the image processing apparatus; an ultrasound endoscope including an ultrasound transducer configured to transmit an ultrasound wave to an observation target, receive an ultrasound signal reflected by the observation target, and output the ultrasound signal to the image processing apparatus; a display configured to display an ultrasound image generated by the image processing apparatus; and an input device configured to receive input of a command signal and transmit the command signal to the image processing apparatus.

An operation method of an image processing apparatus according to the disclosure includes: determining whether a confirmation operation has been performed and, when the confirmation operation has not been performed, terminating processing or, when the confirmation operation has been performed, determining whether a distance between a first representative position of a first pointer and a second representative position of a region of interest is shorter than a predetermined distance, the first pointer having a predetermined shape and being superimposed on an image displayed on a display, the region of interest being set corresponding to a position of the first pointer; and when it is determined that the distance between the first representative position and the second representative position is shorter than the predetermined distance, switching the region of interest so as to be editable.

A non-transitory computer-readable recording medium according to the disclosure is a non-transitory computer-readable recording medium having an executable program recorded therein, the program instructing a processor to execute the following: determining whether a confirmation operation has been performed and, when the confirmation operation has not been performed, terminating processing or, when the confirmation operation has been performed, determining whether a distance between a first representative position of a first pointer and a second representative position of a region of interest is shorter than a predetermined distance, the first pointer having a predetermined shape and being superimposed on an image displayed on a display, the region of interest being set corresponding to a position of the first pointer; and when it is determined that the distance between the first representative position and the second representative position is shorter than the predetermined distance, switching the region of interest so as to be editable.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
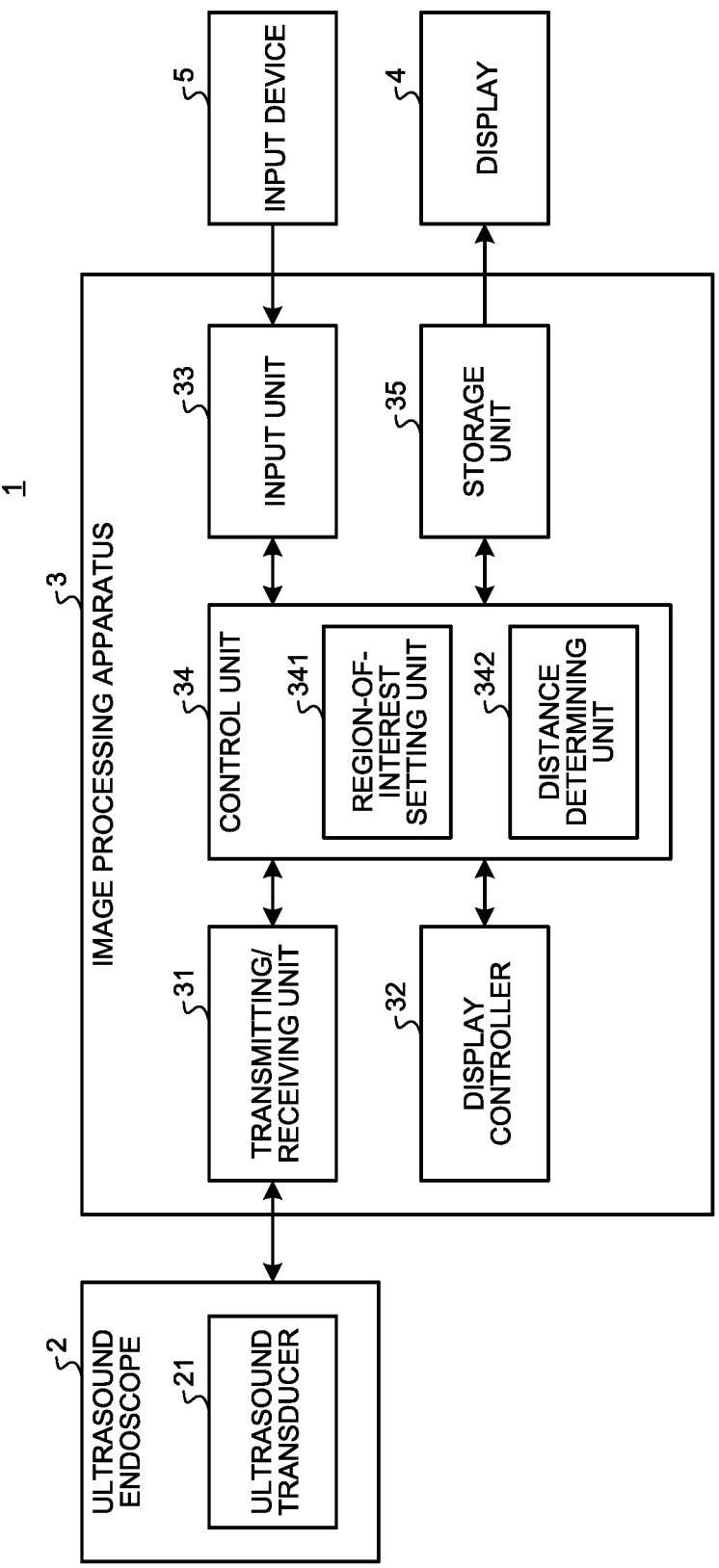
FIG. 1 is a block diagram that illustrates a configuration of an ultrasound diagnosis system including an image processing apparatus according to an embodiment.

With reference to the drawings, an explanation is given below of an embodiment of an image processing apparatus, an ultrasound diagnosis system, an operation method of the image processing apparatus, and an operation program of the image processing apparatus according to the present disclosure. Furthermore, the present disclosure is not limited to the embodiment thereof. In the following embodiment, an explanation is given of a case where multiple regions of interest are set for ultrasound elastography; however, any case is applicable as long as multiple regions of interest are set.

Furthermore, in the description of drawings, the same or corresponding elements are attached with the same reference numeral as appropriate. Furthermore, the drawings are schematic, and it should be noted that the relation between elements in a dimension, the ratio between elements, and the like, differ from reality in some cases. The drawings may sometimes contain the part in which the relation in a dimension or a ratio is different with respect to each other.

FIG. 1 is a block diagram that illustrates a configuration of an ultrasound diagnosis system including the image processing apparatus according to an embodiment. As illustrated in FIG. 1, an ultrasound diagnosis system 1 includes: an ultrasound endoscope 2 that transmits a ultrasound wave to the subject, which is an observation target, and receives an ultrasound wave reflected by the subject; an image processing apparatus 3 that generates an ultrasound image based on an ultrasound wave signal acquired by the ultrasound endoscope 2; a display 4 that displays an ultrasound image generated by the image processing apparatus 3; an input device 5 that receives an input of a command signal for the setting of the observation mode of the image processing apparatus 3, the setting of the observation condition, or the like, and transmits it to the image processing apparatus 3.

At the distal end part of the ultrasound endoscope 2, an ultrasound transducer 21 is provided, which converts an electric pulse signal received from the image processing apparatus 3 into an ultrasound pulse (sound pulse), emits it to the subject, converts an ultrasound echo reflected by the subject into an electric echo signal (ultrasound signal) represented by changes in a voltage, and outputs it. The ultrasound transducer 21 is implemented by using a radial transducer. The ultrasound endoscope 2 may cause the ultrasound transducer 21 to conduct scanning mechanically or may cause it to conduct scanning electronically with a plurality of elements arranged in an array as the ultrasound transducer 21 by electronically switching the elements for transmitting/receiving or by applying a delay for each element in transmitting/receiving.

The ultrasound endoscope 2 typically includes an imaging unit including an optical imaging system and an imaging element, and it is inserted into a digestive tract (esophagus, stomach, duodenum, large intestine) or respiratory apparatus (trachea, bronchi) of the subject so as to capture the digestive tract, the respiratory apparatus, or their periphery organs (pancreas, gallbladder, bile duct, biliary tract, lymph node, mediastinal organ, blood vessel, or the like). Furthermore, the ultrasound endoscope 2 includes a light guide that guides illumination light emitted to the subject during capturing. The distal end part of the light guide reaches the distal end of the insertion unit of the ultrasound endoscope 2 for the subject while the proximal end part thereof is connected to a light source device that generates the illumination light.

The image processing apparatus 3 includes a transmitting/receiving unit 31, a display controller 32, an input unit 33, a control unit 34, and a storage unit 35.

The transmitting/receiving unit 31 transmits and receives an electric signal to and from the imaging unit and the ultrasound transducer 21. The transmitting/receiving unit 31 is electrically connected to the imaging unit to transmit imaging information such as the imaging timing to the imaging unit and receives an imaging signal generated by the imaging unit. Furthermore, the transmitting/receiving unit 31 is electrically connected to the ultrasound transducer 21 to transmit an electrical pulse signal to the ultrasound transducer 21 and receive an echo signal that is an electric reception signal from the ultrasound transducer 21. Specifically, the transmitting/receiving unit 31 generates an electric pulse signal based on the previously set waveform and transmission timing and transmits the generated pulse signal to the ultrasound transducer 21.

The transmitting/receiving unit 31 conducts STC (Sensitivity Time Control) correction to amplify an echo signal having a larger receive depth with a higher amplification factor. The transmitting/receiving unit 31 performs processing such as filtering on the amplified echo signal and then conducts A/D conversion to generate and output time-domain digital high-frequency (RF: Radio Frequency) signal.

The display controller 32 generates endoscope image data based on an imaging signal and ultrasound image data corresponding to an electric echo signal. Furthermore, the display controller 32 superimposes various types of information on endoscope image data and ultrasound image data and outputs them, thereby controlling the display on the display 4. The display controller 32 is implemented by using a CPU (Central Processing Unit), various arithmetic circuits, or the like, having calculation and control functions.

The display controller 32 causes the display 4 to display an ultrasound image on which an ROI pointer serving as a first pointer for setting a region of interest (ROI: Region of Interest) is superimposed. Furthermore, the ROI is used for, for example, setting the region colored in accordance with the rigidity of living tissue in ultrasound elastography. Moreover, the ROI may be used for setting the region for observing the blood flow in the subject by observing the intensity of an ultrasound signal reflected by the contrast agent administered to the subject and conducting TIC (Time Intensity Curve) analysis.

The display controller 32 moves the position of the ROI pointer within the ultrasound image in accordance with the input position input from the input device 5. Furthermore, the display controller 32 causes the display 4 to display the ultrasound image having the ROI superimposed thereon. Furthermore, when a distance determining unit 342 (distance determining circuit) determines that the distance between a first representative position and a second representative position is shorter than a predetermined distance, the display controller 32 switches the ROI pointer to a pointer marker serving as a second pointer different from the ROI pointer for selecting the already set ROI. Here, the first representative position is, for example, the outer periphery of the ROI pointer, the second representative position is, for example, the outer periphery of the already set ROI, and when for example the ROI pointer and the ROI are overlapped with each other (the shortest distance between the outer peripheries is zero), the display controller 32 switches the ROI pointer to the pointer marker. However, the first representative position may be the center position of the ROI pointer, and the second representative position may be the center position of the ROI; thus, the positions of the first representative position and the second representative position are not particularly limited.

Although the ROI pointer is, for example, a circular shape, it may be a square shape, a fan-like shape, or the like, and there is no particular limitation on the shape. Although the pointer marker is, for example, a vertical line and a horizontal line that are perpendicular to each other, it may be an X-shape or a point, and there is no particular limitation on the shape. The center of the circular ROI pointer coincides with the intersection point of the straight lines of the pointer marker, and in the following description, this position is referred to as the center position of the ROI pointer and the pointer marker.

When the ROI pointer and the ROI are overlapped with each other, the display controller 32 switches the indicator of the ROI overlapped with the ROI pointer to the indicator in the selected state that notifies that the ROI is being selected. The selected state indicates the state where any one of the already set ROIs is being selected and notifies the operator that the ROI in the selected state is operated in accordance with the input position input from the input device 5. The ROI in the selected state is highlighted by superimposing a predetermined graphic (e.g., X-shaped line) on the outer periphery of the ROI, displaying a heavy line around the outer periphery of the ROI, or by being displayed in a color different from the one before it is selected.

Furthermore, when the shortest distance between the center position of the pointer marker and the outer periphery of the ROI is smaller than a predetermined distance, and when the confirmation operation for confirming the input position is input to the input device 5, the display controller 32 deforms the ROI in accordance with a movement of the input position that is input after the confirmation operation. Moreover, although the confirmation operation is, for example, an operation to tap the operating screen of the touch-pad of the input device 5, it may be an operation to press the confirmation button disposed outside the touch-pad.

Furthermore, when the center position of the pointer marker is located within the ROI and when a confirmation operation is input, the display controller 32 places the ROI pointer at the region of which the setting as the region of interest has been canceled by a region-of-interest setting unit 341 (region-of-interest setting circuit).

Furthermore, when the distance determining unit 342 determines that the ROI pointer and multiple ROIs are overlapped with each other and determines that the ROIs, which are determined are overlapped with the ROI pointer, are overlapped with each other, the display controller 32 switches the indicator of the previously set ROI among the ROIs overlapped with the ROI pointer to the indicator in the selected state.

Furthermore, when the distance determining unit 342 determines that the ROI pointer and multiple ROIs are overlapped with each other and determines that the ROIs, which are determined are overlapped with the ROI pointer, have an inclusion relation, the display controller 32 switches the indicator of the included ROI among the ROIs overlapped with the ROI pointer to the indicator in the selected state.

Furthermore, when there are two or more inputs of the input position with respect to the input device 5, the display controller 32 causes the display 4 to display an ultrasound image constantly having the ROI pointer superimposed thereon. The two or more inputs of the input position mean that, for example, the operator operates the trackpad of the input device 5 with two fingers. Moreover, it is preferable that, when an operation is performed with two fingers, the center position of the finger with which the touch-pad of the input device 5 is first touched out of the two fingers corresponds to the center position of a ROI pointer p1 and a pointer marker p2. As the center position of the finger with which the touch-pad of the input device 5 is first touched out of the two fingers corresponds to the center position of the ROI pointer p1 and the pointer marker p2, the center position of the ROI pointer p1 and the pointer marker p2 is not shifted when the operator switches from the operation with one finger to the operation with two fingers, whereby the operator's usability is desirable. Moreover, when an operation is performed with two fingers, the center of gravity of the two fingers may correspond to the center position of the ROI pointer p1 and the pointer marker p2.

The input unit 33 receives a command signal input by the input device 5 and receives input of various types of information corresponding to the received command signal. The various types of information include, in addition to command information on the input position or the confirmation operation, the setting of the observation mode, the setting of the observation condition (e.g., the switchover of the gain and the display range, or scrolling command information (the sliding direction and the sliding degree of an ultrasound image)), rotation command information (the rotation direction and the rotation degree of an ultrasound image), and the like.

The control unit 34 performs overall control of the ultrasound diagnosis system 1. The control unit 34 is implemented by using a CPU, various types of arithmetic circuits, or the like, having calculation and control functions. The control unit 34 reads, from the storage unit 35, the information saved and stored in the storage unit 35 and executes various types of arithmetic processing related to the operation method of the image processing apparatus 3, thereby performing the overall control of the image processing apparatus 3. Furthermore, the control unit 34 may be configured by using a CPU, or the like, that is shared by the display controller 32. Moreover, the control unit 34 includes the region-of-interest setting unit 341 and the distance determining unit 342.

The region-of-interest setting unit 341 sets, as the ROI, the region corresponding to the ROI pointer on the ultrasound image when a confirmation operation is input to the input device 5. Furthermore, when the center position of the pointer marker is located within the ROI and when a confirmation operation is input, the region-of-interest setting unit 341 cancels the setting of the region of interest with regard to the ROI including the center position of the pointer marker therein.

The distance determining unit 342 determines whether the ROI pointer and the ROI set by the region-of-interest setting unit 341 are overlapped with each other on the ultrasound image. Furthermore, the distance determining unit 342 determines any distance and positional relationship on an ultrasound image, such as the shortest distance between the center position of the pointer marker and the outer periphery of the ROI, the positional relationship between the center position of the pointer marker and the outer periphery of the ROI, as to whether the ROIs are overlapped with each other, as to whether the ROIs have an inclusion relation with respect to each other, or the like.

Furthermore, after the region-of-interest setting unit 341 sets the ROI, the control unit 34 calculates the amount of displacement of the living tissue in the ROI during ultrasound elastography, and the display controller 32 causes the information about the rigidity of the living tissue to be displayed on an ultrasound image 41. Furthermore, after the region-of-interest setting unit 341 sets the ROI, the control unit 34 may conduct TIC analysis on the inside of the ROI in the contrast-enhanced mode and cause the velocity information, or the like, on the contrast agent flowing in or out in the subject to be displayed.

The storage unit 35 stores data, and the like, including various programs for operating the ultrasound diagnosis system 1, various parameters needed to operate the ultrasound diagnosis system 1, and the like. The storage unit 35 stores, for example, the initial position (sound ray number) of the writing position of an ultrasound image (the transmission start position of an ultrasound wave).

Furthermore, the storage unit 35 stores various programs including the operation program for executing the operation method of the ultrasound diagnosis system 1. The operation program may be widely distributed by being stored in a storage medium readable by a computer, such as a hard disk, a flash memory, a CD-ROM, a DVD-ROM, or a flexible disk. Furthermore, the above-described various programs may be acquired by being downloaded via a communication network. The communication network mentioned here may be implemented by, for example, the existing public network, a LAN (Local Area Network), or a WAN (Wide Area Network), and it may be wired or wireless.

The storage unit 35 having the above configuration is implemented by using, for example, a ROM (Read Only Memory) having various programs, and the like, previously installed therein, or a RAM (Random Access Memory) storing calculation parameters, data, and the like, for each process.

The display 4 is connected to the image processing apparatus 3. The display 4 is configured by using a display panel formed of a liquid crystal, organic EL (Electro Luminescence), or the like. The display 4 displays, for example, an ultrasound image output from the image processing apparatus 3 or various types of information related to the operation.

The input device 5 includes a touch-pad or a touch panel that detects the contact with the operator's finger, or the like. The input device 5 is electrically connected to the image processing apparatus 3 via a cable to output, to the input unit 33, a signal, or the like, for a command input to the touch-pad. Further, the input device 5 may be implemented by using a keyboard, a trackball, a mouse, a joystick, or the like, or with the combination thereof.

When the touch-pad is touched with a contact object such as the operator's finger, the input device 5 uses the contact sensor to detect the contact position and outputs it to the image processing apparatus 3. Furthermore, when the contact object moves while being in contact with the touch-pad, the moving direction and the movement distance are detected and output to the image processing apparatus 3. Furthermore, the number of contact positions is detected and output to the image processing apparatus 3. Based on the received information, the image processing apparatus 3 performs the signal processing corresponding to the input contact position, the moving direction of the contact position, the movement distance, and the number. Then, the image processing apparatus 3 controls the image to be displayed on the display 4 based on, for example, the input position defined in accordance with the received information.

Figure 2:
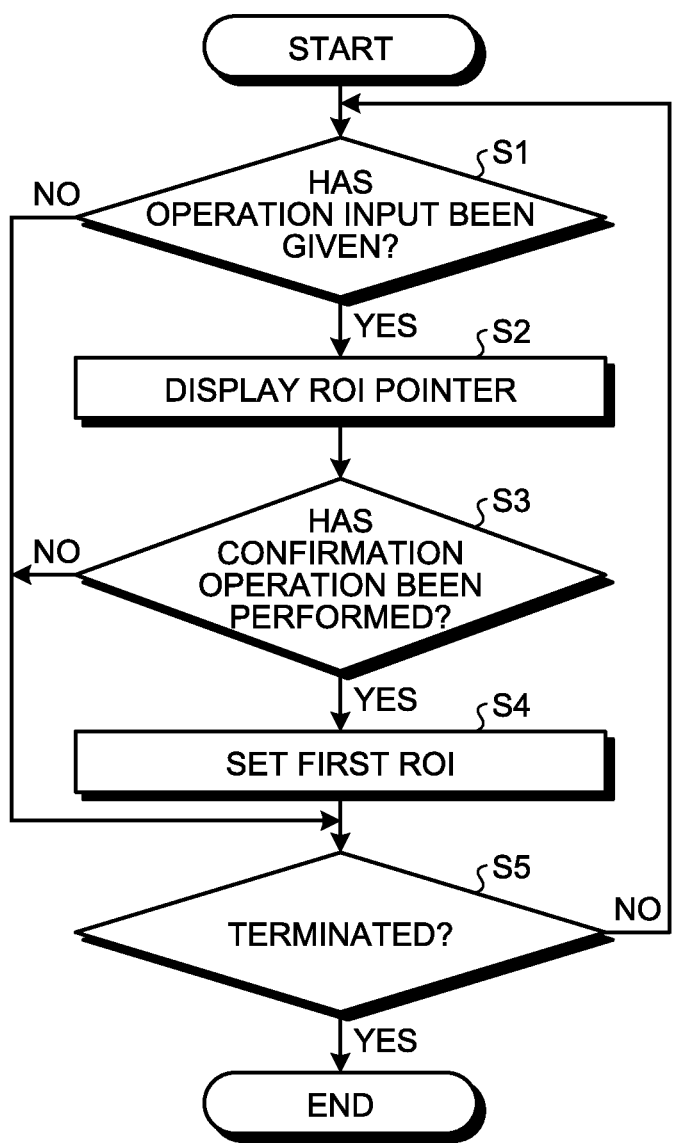
FIG. 2 is a flowchart that illustrates an operation in the ultrasound diagnosis system illustrated in FIG. 1 in a state where no ROI has been set.
Figure 3:
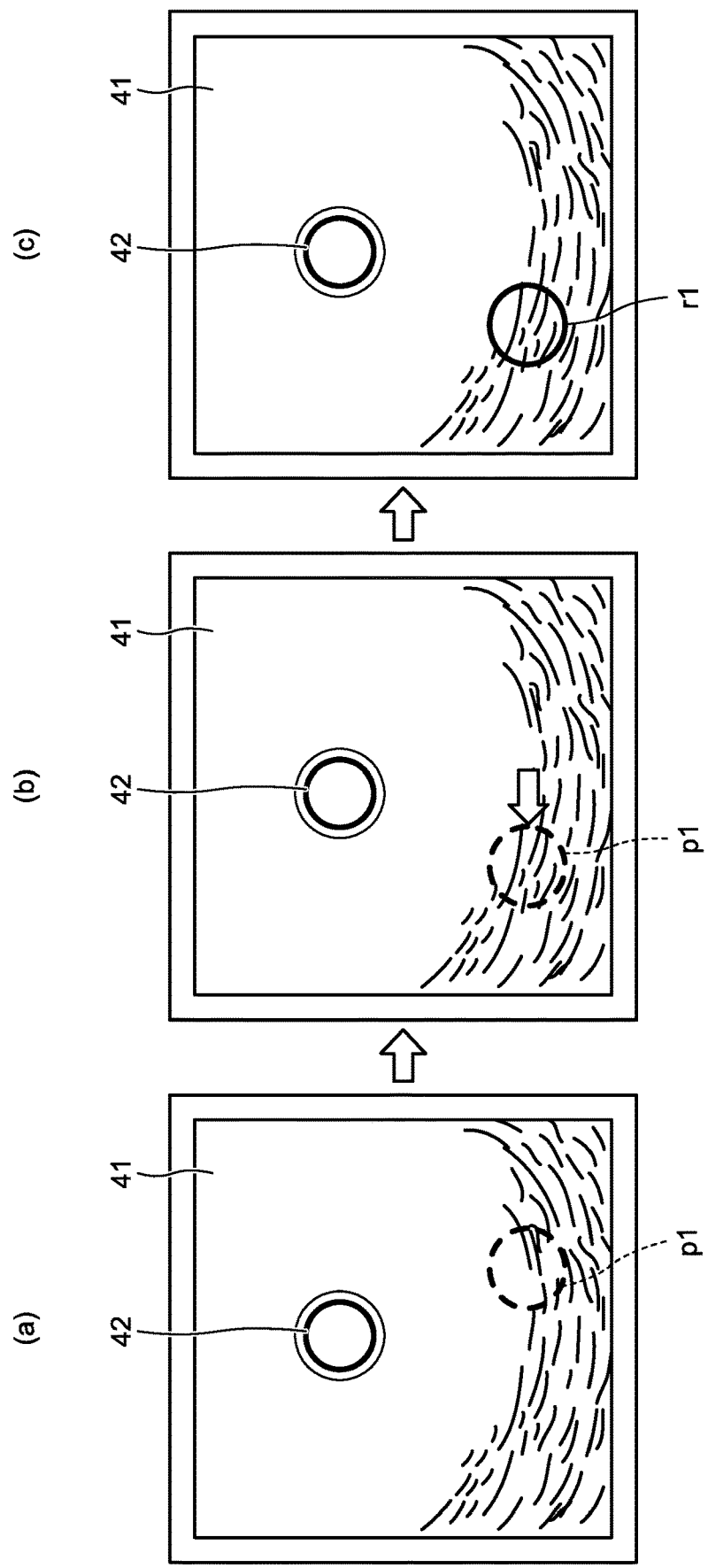
FIG. 3 is a diagram that illustrates an image displayed on a display when a first ROI is set.

Next, an operation of the ultrasound diagnosis system 1 is explained. First, an explanation is given of an operation for setting a primary ROI (first ROI) in a state where no ROI has been set on the ultrasound image. FIG. 2 is a flowchart that illustrates an operation in the ultrasound diagnosis system illustrated in FIG. 1 in a state where no ROI has been set. FIG. 3 is a diagram that illustrates an image displayed on the display when the first ROI is set. The ultrasound image 41 illustrated in FIG. 3 displays an ultrasound transducer 42 corresponding to the ultrasound transducer 21 of the ultrasound endoscope 2.

First, as illustrated in FIG. 2, the control unit 34 determines whether an operation input has been given (Step S1). Specifically, the control unit 34 determines whether an operation input performed on the touch-pad of the input device 5 by the operator has been input via the input unit 33.

When the control unit 34 determines that an operation input has been given (Step S1: Yes), the display controller 32 causes the display 4 to display the ultrasound image 41 having the ROI pointer p1 superimposed thereon in accordance with the operation input (Step S2). As illustrated in (a) of FIG. 3, the display controller 32 causes the ROI pointer p1 to be displayed by, for example, a dashed line at the position corresponding to the operation input within the ultrasound image 41. Furthermore, as illustrated in (b) of FIG. 3, when the contact position of the operator's finger on the touch-pad of the input device 5 moves, the display controller 32 moves the position of the ROI pointer p1 superimposed on the ultrasound image 41 such that it follows the movement of the input position that is input from the input device 5 via the input unit 33.

Then, the control unit 34 determines whether a confirmation operation has been performed (Step S3). Specifically, the control unit 34 determines whether the operator has performed the confirmation operation on the touch-pad of the input device 5 and the signal representing the confirmation operation has been input via the input unit 33.

When the control unit 34 determines that the confirmation operation has been performed (Step S3: Yes), the region-of-interest setting unit 341 sets the region corresponding to the ROI pointer p1 within the ultrasound image 41 as the region of interest (a first ROI r1) (Step S4). Here, as illustrated in (c) of FIG. 3, the display controller 32 causes the first ROI r1 to be displayed by, for example, a solid line as the region set as the region of interest.

Furthermore, after the region-of-interest setting unit 341 sets the first ROI r1 as the region of interest, the control unit 34 calculates, for example, the amount of displacement of the living tissue within the first ROI r1, and the display controller 32 causes the display 4 to display the ultrasound image 41 having the information about the rigidity of the living tissue superimposed thereon in accordance with the amount of displacement calculated by the control unit 34.

Then, the control unit 34 determines whether a termination command input has been received (Step S5), and when the control unit 34 determines that a termination command input has been received (Step S5: Yes), the sequence of processes is terminated. Conversely, when the control unit 34 determines that a termination command input has not been received (Step S5: No), the process returns to Step S1 and continues.

Furthermore, when an operation is not performed for more than a predetermined time period at the step (Step S1) for determining whether an operation input has been given and at the step (Step S3) for determining whether a confirmation operation has been performed, a termination determination is made at Step S5 so that the sequence of processes is terminated or continued.

Figure 4:
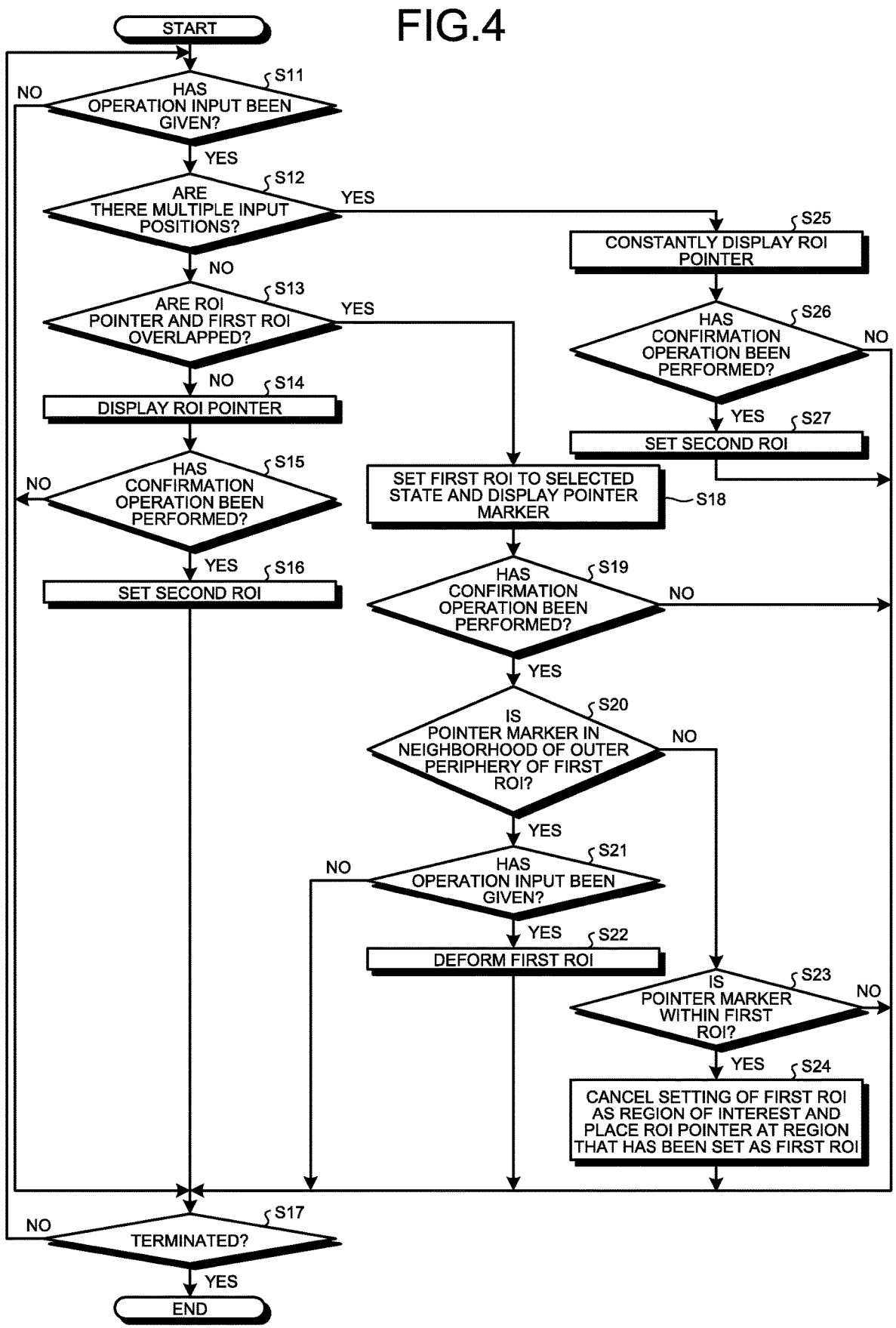
FIG. 4 is a flowchart that illustrates an operation in the ultrasound diagnosis system illustrated in FIG. 1 in a state where the first ROI has been set.

Next, an explanation is given of an operation in a state where the first ROI r1 has been set. FIG. 4 is a flowchart that illustrates an operation in the ultrasound diagnosis system illustrated in FIG. 1 in a state where the first ROI has been set. That is, it corresponds to the case where an operation is further performed after the first ROI r1 is set by executing Step S1 to Step S4 in the flowchart illustrated in FIG. 2; however, in the flowchart of FIG. 4, the operation before the first ROI r1 is set is omitted.

After the first ROI r1 is set, as illustrated in FIG. 4, the control unit 34 determines whether an operation input has been given (Step S11). When the control unit 34 determines that an operation input has been given (Step S11: Yes), the control unit 34 determines whether there are multiple input positions that are input from the input device 5 (Step S12). Specifically, the control unit 34 determines whether the operator has performed an operation on the touch-pad of the input device 5 with one finger or two or more fingers on the basis of the input signal from the input unit 33.

The control unit 34 determines that there are not multiple input positions that are input from the input device 5 (Step S12: No), the distance determining unit 342 determines whether the ROI pointer p1 and the first ROI r1 set by the region-of-interest setting unit 341 are overlapped with each other (Step S13).

Figure 5:
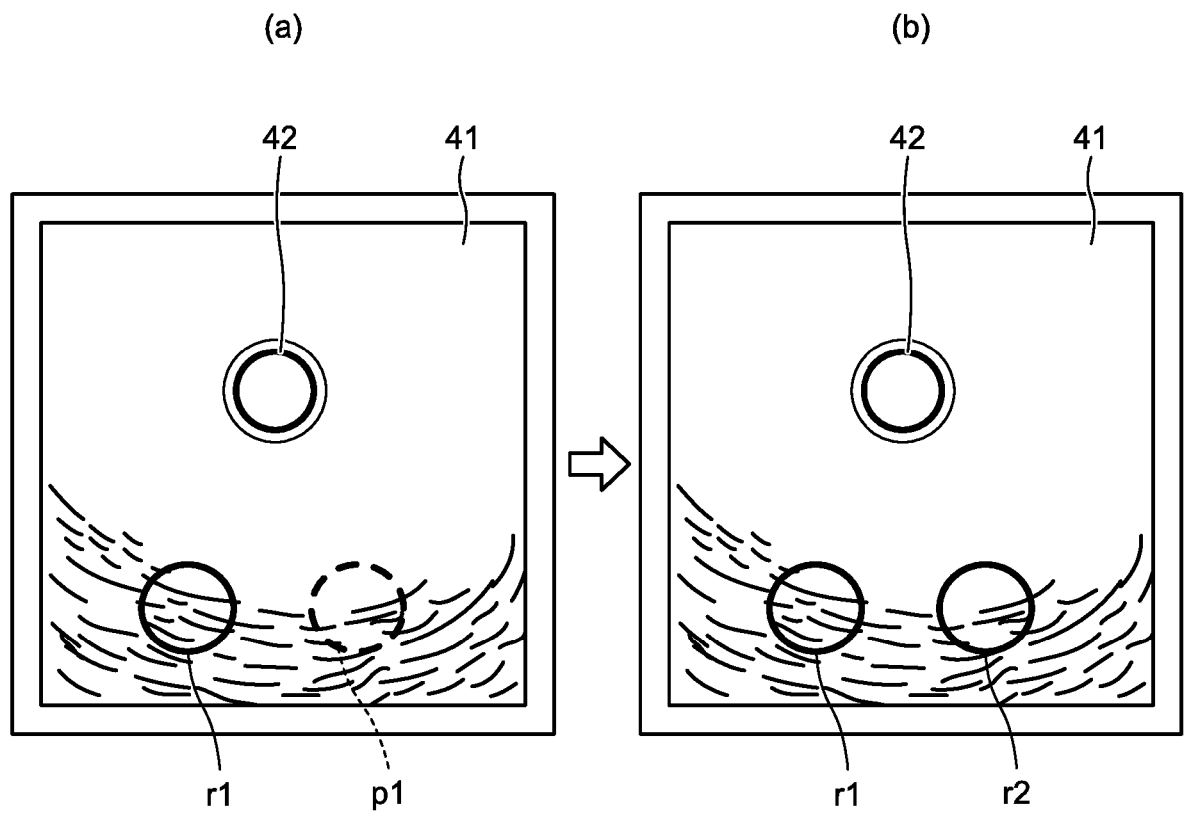
FIG. 5 is a diagram that illustrates an image displayed on the display when a second ROI is set.

When the distance determining unit 342 determines that the ROI pointer p1 and the first ROI r1 are not overlapped with each other (Step S13: No), the display controller 32 causes the display 4 to display the ultrasound image 41 having the ROI pointer p1 superimposed thereon in accordance with the operation input (Step S14). FIG. 5 is a diagram that illustrates an image displayed on the display when a second ROI is set. As illustrated in (a) of FIG. 5, the display controller 32 causes the ROI pointer p1 to be displayed in, for example, a dashed line at the position corresponding to the operation input within the ultrasound image 41. Furthermore, when the contact position of the operator's finger on the touch-pad of the input device 5 moves, the display controller 32 moves the position of the ROI pointer p1 superimposed on the ultrasound image 41 such that it follows the movement of the input position that is input from the input device 5.

Then, the control unit 34 determines whether the confirmation operation has been performed (Step S15). When the control unit 34 determines that the confirmation operation has been performed (Step S15: Yes), the region-of-interest setting unit 341 sets the region corresponding to the ROI pointer p1 within the ultrasound image 41 as the region of interest (a second ROI r2) (Step S16). Here, as illustrated in (b) of FIG. 5, the display controller 32 causes the second ROI r2 set in the ultrasound image 41 to be displayed in, for example, a solid line as the region set as the region of interest. Therefore, it is possible to set the second ROI r2 without performing a complicated operation.

Then, the control unit 34 determines whether a termination command input has been received (Step S17), and when the control unit 34 determines that a termination command input has been received (Step S17: Yes), the sequence of processes is terminated. Conversely, when the control unit 34 determines that no termination command input has been received (Step S17: No), the process returns to Step S11 and continues.

Figure 6:
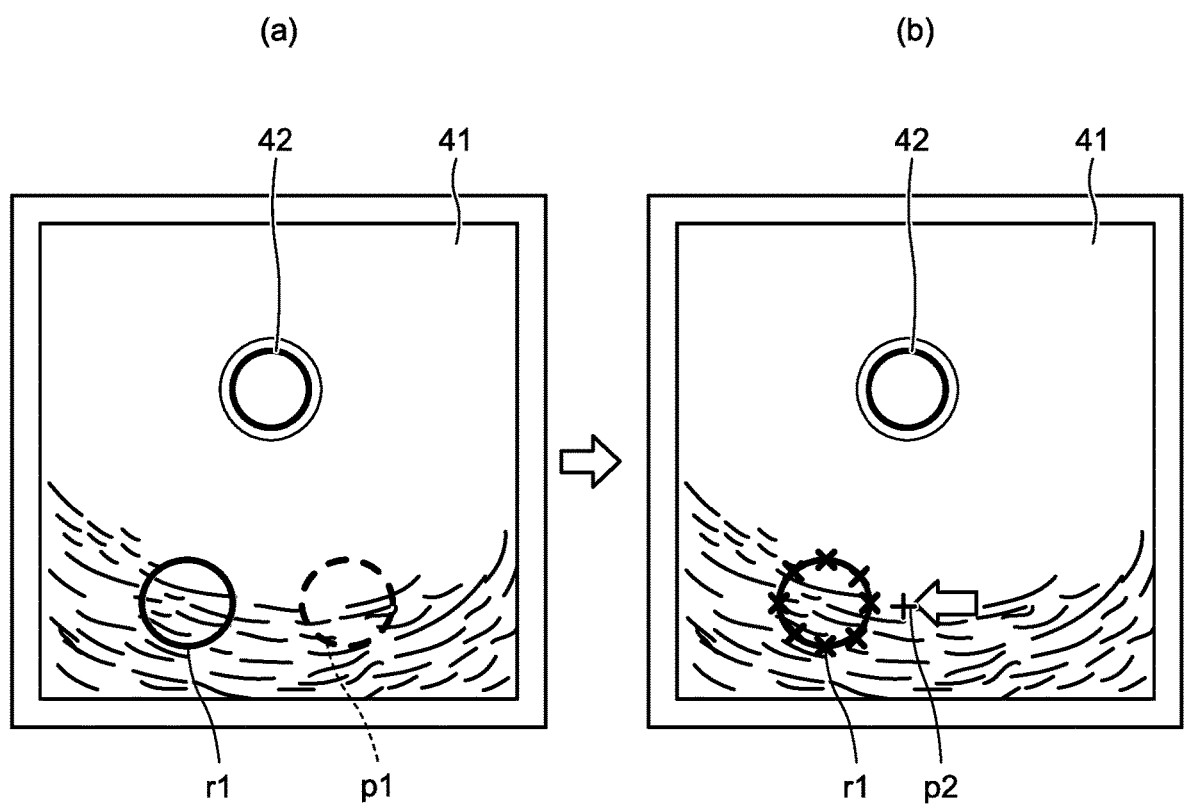
FIG. 6 is a diagram that illustrates an image displayed on the display when a ROI pointer and the first ROI are overlapped with each other.

When the distance determining unit 342 determines that the ROI pointer p1 and the first ROI r1 are overlapped with each other at Step S13 (Step S13: Yes), the display controller 32 switches the indicator of the first ROI r1 to the indicator in the selected state and causes the display 4 to display the ultrasound image 41 having the pointer marker p2 superimposed thereon (Step S18). FIG. 6 is a diagram that illustrates an image displayed on the display when the ROI pointer and the first ROI are overlapped with each other. As illustrated in FIG. 6, when the input position, input from the input device 5, moves from the position ((a) of FIG. 6) where the ROI pointer p1 and the first ROI r1 are not overlapped with each other to the position ((b) of FIG. 6) where the ROI pointer p1 and the first ROI r1 are overlapped with each other, the display controller 32 switches the indicator of the first ROI r1 to the indicator in the selected state and switches the ROI pointer p1 to the pointer marker p2. Furthermore, as the selected state, FIG. 6 illustrates an example where the X-shaped indicator representing the selected state is displayed on the outer periphery of the first ROI r1 in a superimposed manner.

Then, the control unit 34 determines whether a confirmation operation has been performed (Step S19). When the control unit 34 determines that a confirmation operation has been performed (Step S19: Yes), the distance determining unit 342 determines whether the center position of the pointer marker p2 is in the neighborhood of the outer periphery of the first ROI r1 (Step S20).

When the distance determining unit 342 determines that the center position of the pointer marker p2 is in the neighborhood of the outer periphery of the first ROI r1 (Step S20: Yes), the control unit 34 determines whether an operation input has been given (Step S21).

Figure 7:
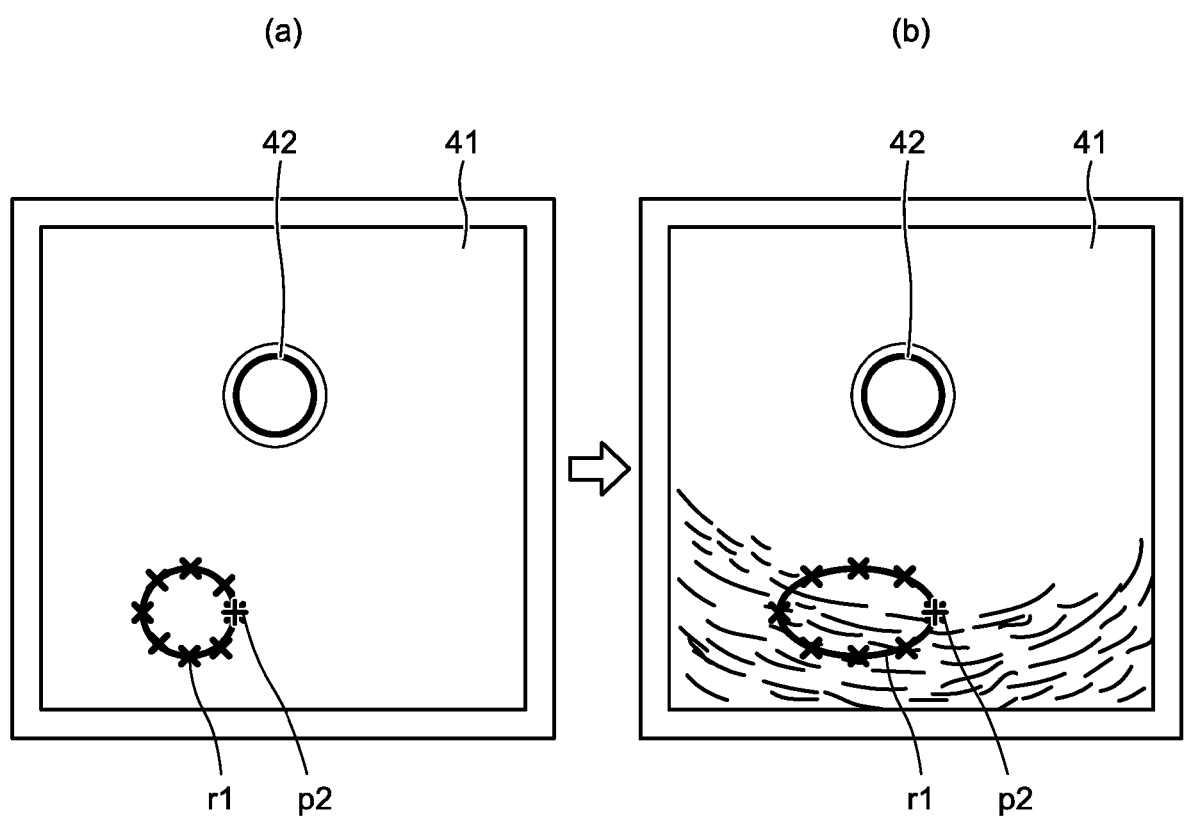
FIG. 7 is a diagram that illustrates an image displayed on the display when the first ROI is deformed.

When the control unit 34 determines that an operation input has been given (Step S21: Yes), the display controller 32 deforms the first ROI r1 in accordance with a movement of the input position corresponding to the operation input (Step S22). FIG. 7 is a diagram that illustrates an image displayed on the display when the first ROI is deformed. As illustrated in (a) of FIG. 7, when the center position of the pointer marker p2 is located in the neighborhood of the outer periphery of the first ROI r1 in the selected state and when a confirmation operation is input, the first ROI r1 is deformed in accordance with a movement of the input position as illustrated in (b) of FIG. 7. Thus, the first ROI r1 may be deformed without performing a complicated operation. Then, a termination determination is made at Step S17, and the process is terminated or continued.

When the distance determining unit 342 determines that the center position of the pointer marker p2 is not in the neighborhood of the outer periphery of the first ROI r1 at Step S20 (Step S20: No), the distance determining unit 342 determines whether the center position of the pointer marker p2 is located within the first ROI r1 (Step S23).

Figure 8:
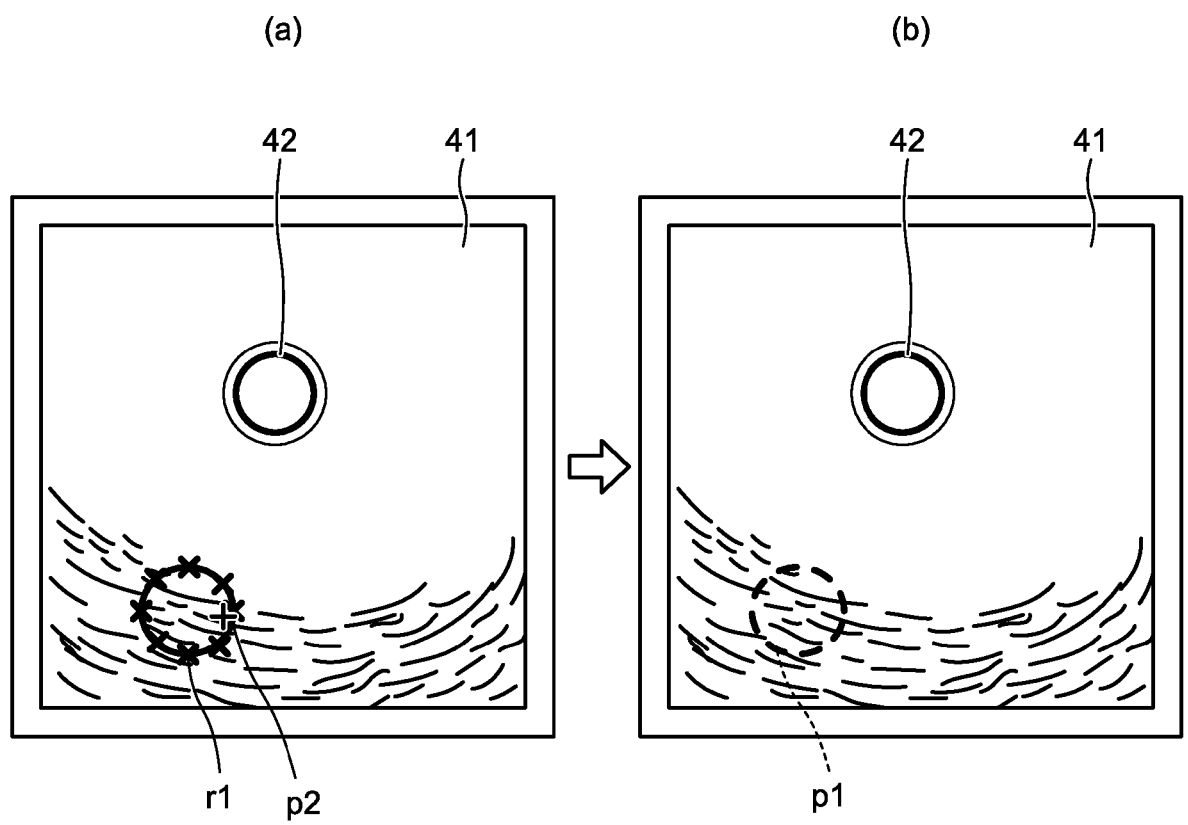
FIG. 8 is a diagram that illustrates the image displayed on the display when the setting of the first ROI as the region of interest is canceled.

When the distance determining unit 342 determines that the center position of the pointer marker p2 is located within the first ROI r1 (Step S23: Yes), the region-of-interest setting unit 341 cancels the setting of the first ROI r1 as the region of interest, and the display controller 32 places the ROI pointer p1 at the region that has been set as the first ROI r1 (Step S24). FIG. 8 is a diagram that illustrates the image displayed on the display when the setting of the first ROI as the region of interest is canceled. As illustrated in (a) of FIG. 8, when the center position of the pointer marker p2 is located within the first ROI r1 and when a confirmation operation is input, the indicator representing the first ROI r1 is deleted and the ROI pointer p1 is displayed at the region that has been set as the first ROI r1, as illustrated in (b) of FIG. 8. By moving the ROI pointer p1 from this state, the first ROI r1 may be set again at any position. In other words, the first ROI r1 may be moved without performing a complicated operation. Then, a termination determination is made at Step S17, and the process is terminated or continued.

When the distance determining unit 342 determines that the center position of the pointer marker p2 is not located within the first ROI r1 at Step S23 (Step S23: No), a termination determination is made at Step S17, and the process is terminated or continued.

When the control unit 34 determines that there are multiple input positions that are input from the input device 5 at Step S12 (Step S12: Yes), the display controller 32 causes the display 4 to display the ultrasound image 41 constantly having the ROI pointer p1 superimposed thereon at the position corresponding to the operation input (Step S25).

Figure 9:
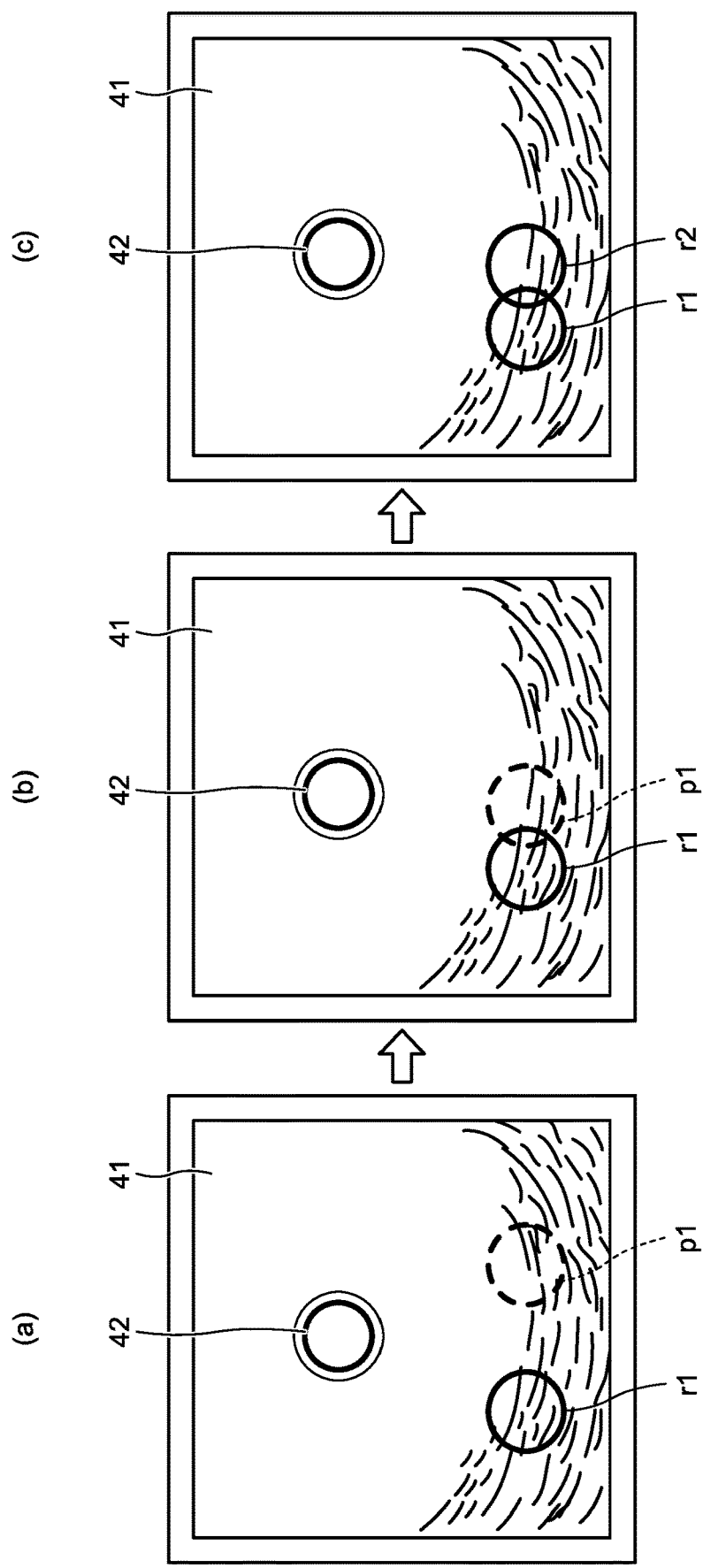
FIG. 9 is a diagram that illustrates the image displayed on the display when a second ROI is set by being overlapped with the first ROI.

Then, the control unit 34 determines whether a confirmation operation has been performed (Step S26). When the control unit 34 determines that a confirmation operation has been performed (Step S26: Yes), the region-of-interest setting unit 341 sets the region corresponding to the ROI pointer p1 within the ultrasound image 41 as the region of interest (the second ROI r2) (Step S27). FIG. 9 is a diagram that illustrates the image displayed on the display when the second ROI is set by being overlapped with the first ROI. In a case where the operator makes an operation input with two or more fingers, even though the ROI pointer p1 is moved from the state ((a) of FIG. 9) where the ROI pointer p1 and the first ROI r1 are not overlapped with each other to the state ((b) of FIG. 9) where the ROI pointer p1 and the first ROI r1 are overlapped with each other, the display controller 32 continuously causes the display 4 to display the ultrasound image 41 constantly having the ROI pointer p1 superimposed thereon. Then, when the ROI pointer p1 and the first ROI r1 are overlapped with each other and when a confirmation operation is input, the region-of-interest setting unit 341 sets the region corresponding to the ROI pointer p1 within the ultrasound image 41 as the region of interest (the second ROI r2). At this time, as illustrated in (c) of FIG. 9, the display controller 32 causes the second ROI r2 set in the ultrasound image 41 to be displayed in, for example, a solid line as the region that is set as the region of interest. In other words, it is possible to set the region overlapped with the first ROI r1 as the region of interest (the second ROI r2) without inconvenience by the operator performing an operation with two fingers. Then, a termination determination is made at Step S17, and the process is terminated or continued.

Furthermore, when an operation is not performed for more than a predetermined time period at the step (Steps S11, S21) for determining whether an operation input has been given and the step (Steps S15, S19, S26) for determining whether a confirmation operation has been performed, a termination determination is made at Step S17 so that the sequence of processes is terminated or continued.

Next, an explanation is given of an operation when two or more ROIs are set. FIG. 10 to FIG. 16 are flowcharts that illustrate an operation in the ultrasound diagnosis system illustrated in FIG. 1 when two ROIs are set. FIG. 11 to FIG. 16 are flowcharts that illustrate an operation after A1 to A6 in FIG. 10. That is, they correspond to the case where an operation is further performed after the first ROI r1 and the second ROI r2 are set, as is the case with the flowcharts illustrated in FIG. 2 and FIG. 4; however, the operation before the first ROI r1 and the second ROI r2 are set is omitted from the flowchart of FIG. 10.

Figure 10:
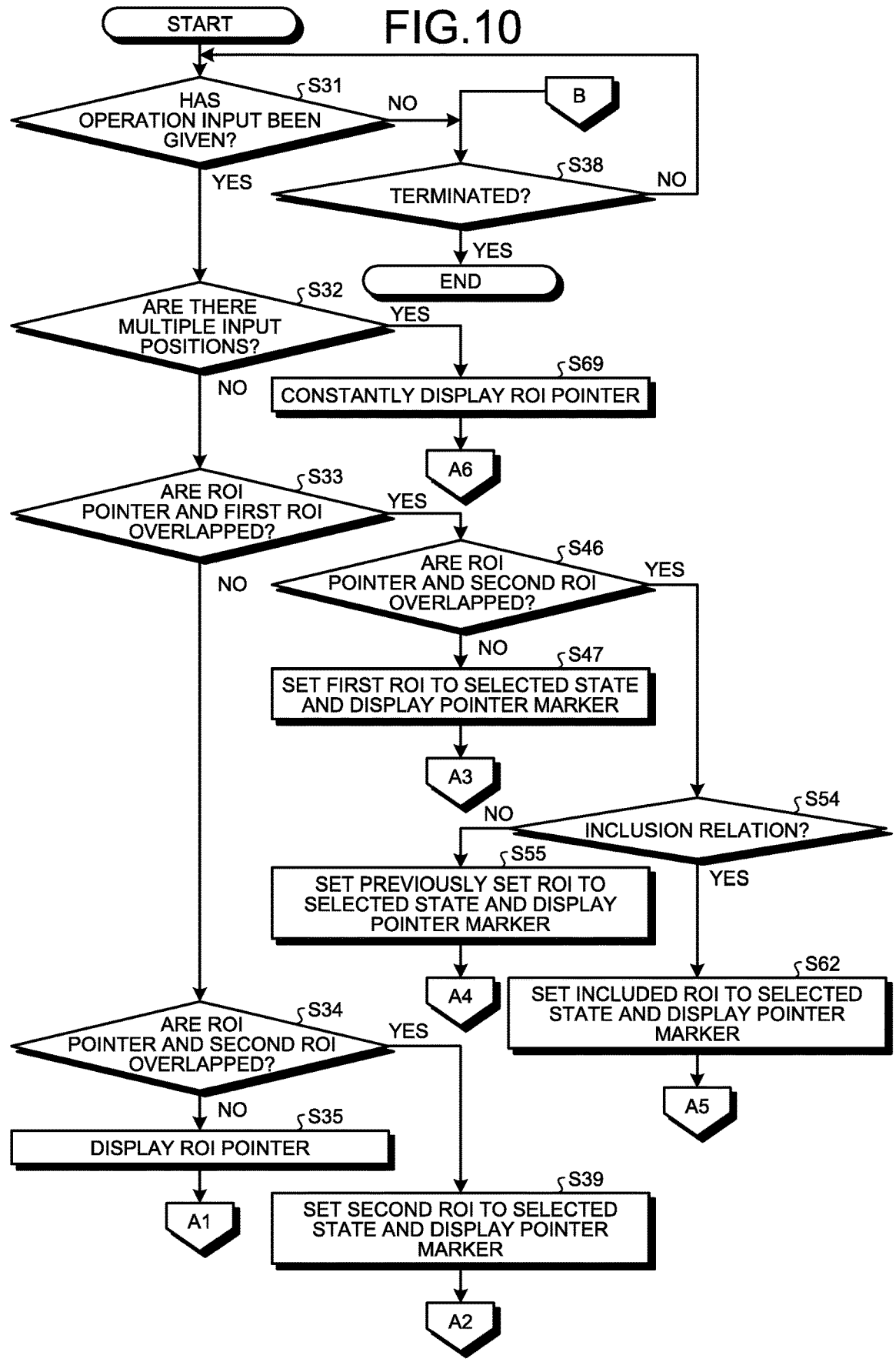
FIG. 10 is a flowchart that illustrates an operation in the ultrasound diagnosis system illustrated in FIG. 1 when two ROIs are set.

After the first ROI r1 and the second ROI r2 are set, the control unit 34 determines whether an operation input has been given (Step S31), as illustrated in FIG. 10. When the control unit 34 determines that an operation input has been given (Step S31: Yes), the control unit 34 determines whether there are multiple input positions input from the input device 5 (Step S32).

When the control unit 34 determines that there are not multiple input positions input from the input device 5 (Step S32: No), the distance determining unit 342 determines whether the ROI pointer p1 and the first ROI r1 are overlapped with each other (Step S33).

When the distance determining unit 342 determines that the ROI pointer p1 and the first ROI r1 are not overlapped with each other (Step S33: No), the distance determining unit 342 determines whether the ROI pointer p1 and the second ROI r2 are overlapped with each other (Step S34).

When the distance determining unit 342 determines that the ROI pointer p1 and the second ROI r2 are not overlapped with each other (Step S34: No), the display controller 32 causes the display 4 to display the ultrasound image 41 having the ROI pointer p1 superimposed thereon in accordance with the operation input (Step S35).

Figure 11:
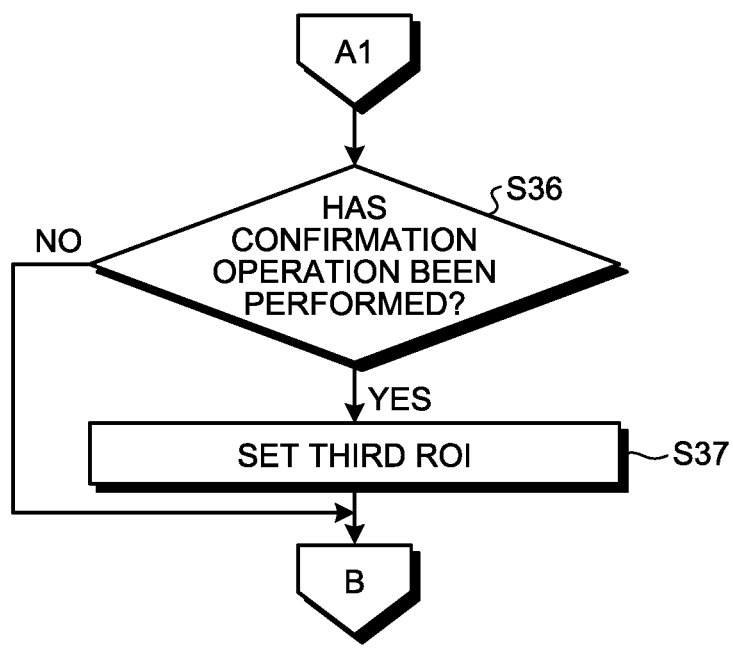
FIG. 11 is a flowchart that illustrates an operation in the ultrasound diagnosis system illustrated in FIG. 1 when two ROIs are set.
Figure 17:
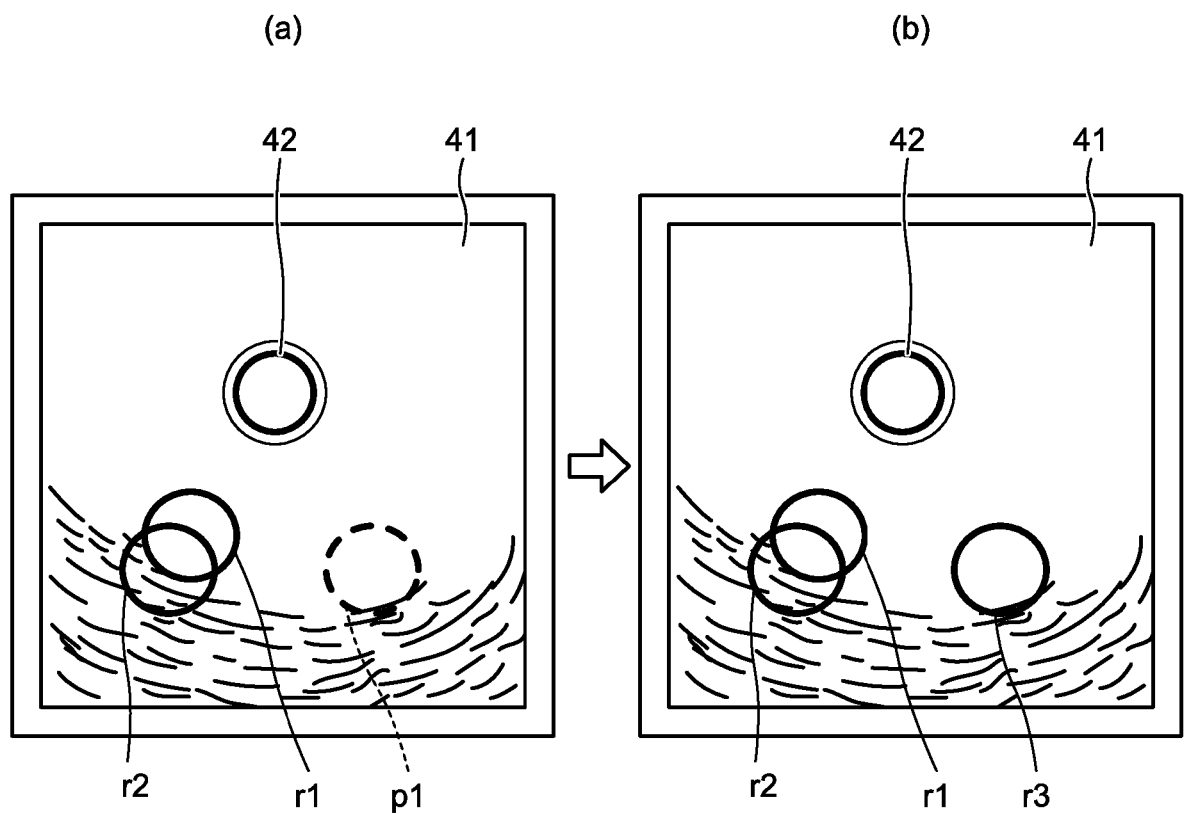
FIG. 17 is a diagram that illustrates the image displayed on the display when a third ROI is set.

Then, the process transitions from A1 to FIG. 11, and the control unit 34 determines whether a confirmation operation has been performed (Step S36). When the control unit 34 determines that a confirmation operation has been performed (Step S36: Yes), the region-of-interest setting unit 341 sets the region corresponding to the ROI pointer p1 in the ultrasound image 41 as the region of interest (a third ROI r3) (Step S37). FIG. 17 is a diagram that illustrates the image displayed on the display when the third ROI is set. As illustrated in (a) of FIG. 17, when a confirmation operation is input in a state where the ROI pointer p1 is not overlapped with the first ROI r1 and the second ROI r2, the region-of-interest setting unit 341 sets the region corresponding to the ROI pointer p1 on the ultrasound image 41 as the region of interest (the third ROI r3), and the display controller 32 causes the third ROI r3 set in the ultrasound image 41 to be displayed in, for example, a solid line as the region set as the region of interest, as illustrated in (b) of FIG. 17. Therefore, the third ROI r3 may be set without inconvenience.

Then, the process returns to FIG. 10 from B so that the control unit 34 determines whether a termination command input has been given (Step S38) and, when the control unit 34 determines that a termination command input has been given (Step S38: Yes), the sequence of processes is terminated. Conversely, when the control unit 34 determines that no termination command input has been given (Step S38: No), the process returns to Step S31 and continues.

At Step S34 in FIG. 10, the distance determining unit 342 determines that the ROI pointer p1 and the second ROI r2 are overlapped with each other (Step S34: Yes), the display controller 32 switches the indicator of the second ROI r2 to the indicator in the selected state and causes the display 4 to display the ultrasound image 41 having the pointer marker p2 superimposed thereon (Step S39).

Figure 12:
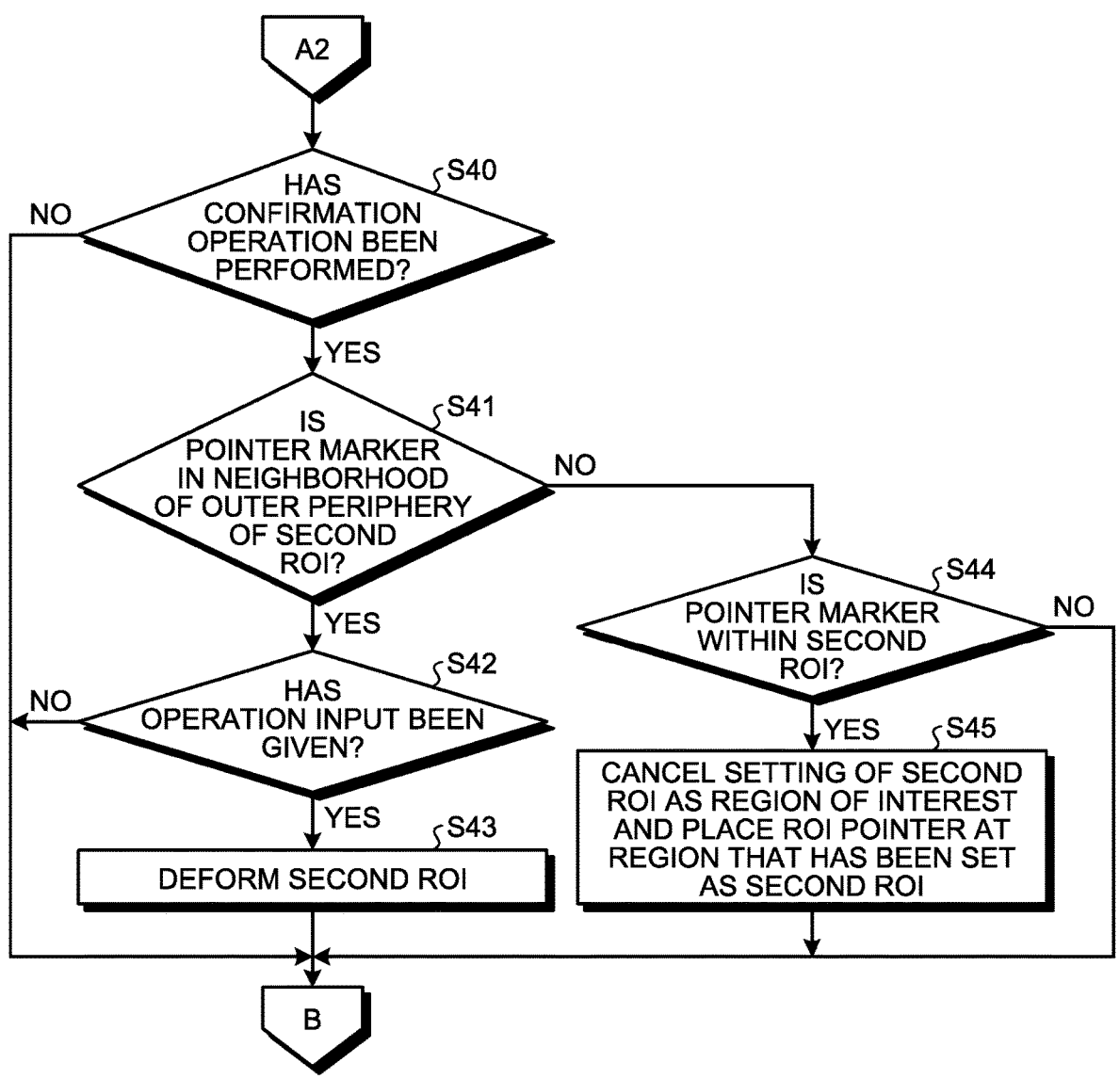
FIG. 12 is a flowchart that illustrates an operation in the ultrasound diagnosis system illustrated in FIG. 1 when two ROIs are set.

Then, the process transitions from A2 to FIG. 12, and the control unit 34 determines whether a confirmation operation has been performed (Step S40). When the control unit 34 determines that a confirmation operation has been performed (Step S40: Yes), the distance determining unit 342 determines whether the center position of the pointer marker p2 is in the neighborhood of the outer periphery of the second ROI r2 (Step S41).

When the distance determining unit 342 determines that the center position of the pointer marker p2 is in the neighborhood of the outer periphery of the second ROI r2 (Step S41: Yes), the control unit 34 determines whether an operation input has been given (Step S42).

Figure 18:
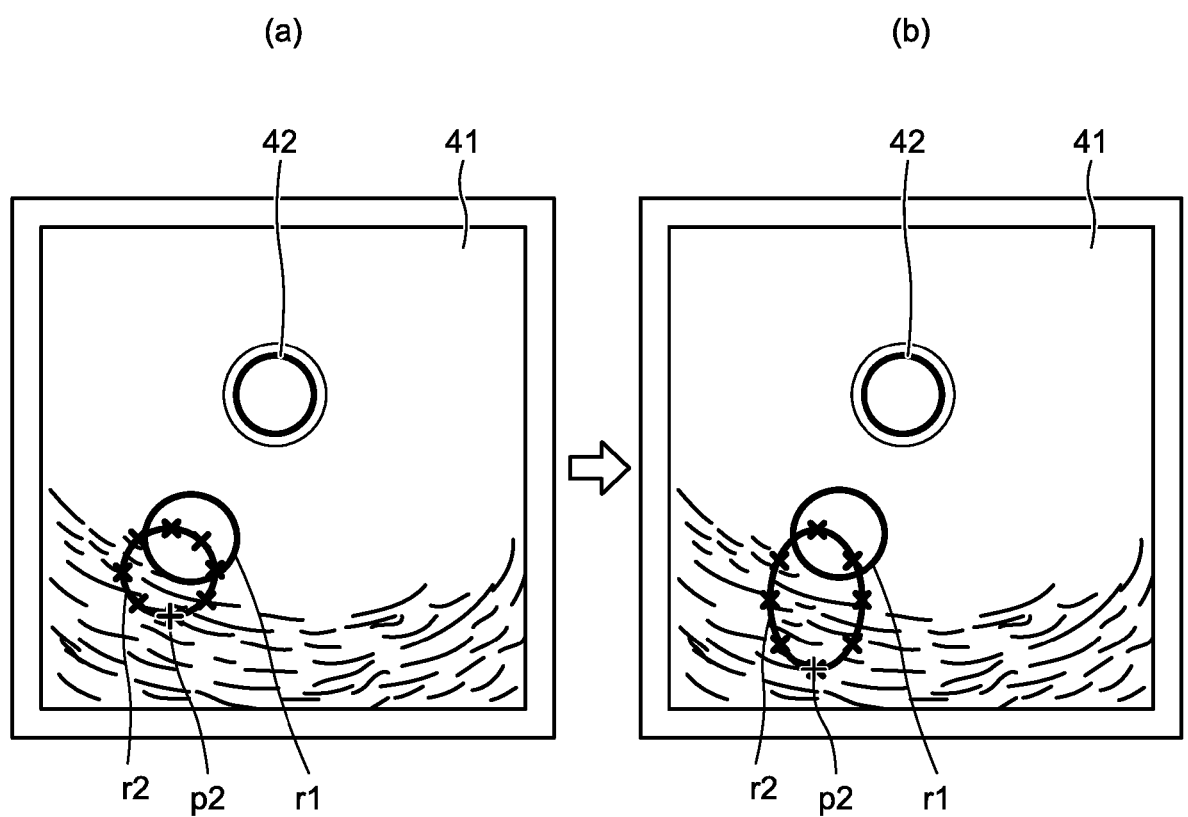
FIG. 18 is a diagram that illustrates the image displayed on the display when the second ROI is deformed.

When the control unit 34 determines that an operation input has been given (Step S42: Yes), the display controller 32 deforms the second ROI r2 in accordance with a movement of the input position corresponding to the operation input (Step S43). FIG. 18 is a diagram that illustrates the image displayed on the display when the second ROI is deformed. As illustrated in (a) of FIG. 18, when the center position of the pointer marker p2 is located in the neighborhood of the outer periphery of the second ROI r2 in the selected state and when a confirmation operation is input, the second ROI r2 is deformed in accordance with a movement of the input position, as illustrated in (b) of FIG. 18. Therefore, the second ROI r2 may be deformed without inconvenience. Then, the process returns to FIG. 10 from B so that a termination determination is made at Step S38, and the process is terminated or continued.

When the distance determining unit 342 determines that the center position of the pointer marker p2 is not in the neighborhood of the outer periphery of the second ROI r2 at Step S41 of FIG. 12 (Step S41: No), the distance determining unit 342 determines whether the center position of the pointer marker p2 is within the second ROI r2 (Step S44).

Figure 19:
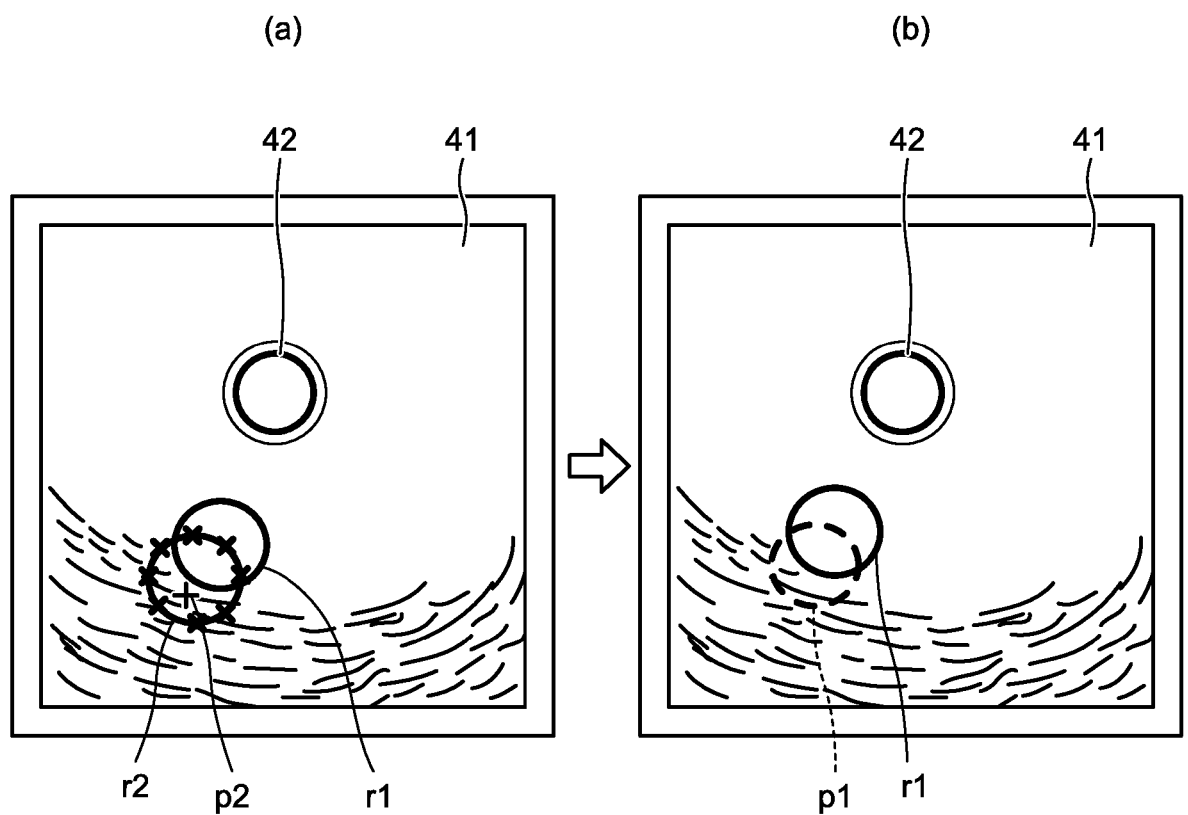
FIG. 19 is a diagram that illustrates the image displayed on the display when the setting of the second ROI as the region of interest is canceled.

When the distance determining unit 342 determines that the center position of the pointer marker p2 is within the second ROI r2 (Step S44: Yes), the region-of-interest setting unit 341 cancels the setting of the second ROI r2 as the region of interest, and the display controller 32 places the ROI pointer p1 at the region that has been set as the second ROI r2 (Step S45). FIG. 19 is a diagram that illustrates the image displayed on the display when the setting of the second ROI as the region of interest is canceled. As illustrated in (a) of FIG. 19, when the center position of the pointer marker p2 is located within the second ROI r2 and when a confirmation operation is input, the indicator representing the second ROI r2 is deleted, and the ROI pointer p1 is displayed at the region that has been set as the second ROI r2, as illustrated in (b) of FIG. 19. By moving the ROI pointer p1 from this state, the second ROI r2 may be set again at any position. In other words, the second ROI r2 may be moved without inconvenience. Furthermore, in this state, by moving the ROI pointer p1 out of the ultrasound image 41, the set second ROI r2 may be deleted. Then, the process returns to FIG. 10 from B so that a termination determination is made at Step S38, and the process is terminated or continued.

When the distance determining unit 342 determines that the center position of the pointer marker p2 is not within the second ROI r2 at Step S44 of FIG. 12 (Step S44: No), the process returns to FIG. 10 from B so that a termination determination is made at Step S38, and the process is terminated or continued.

When the distance determining unit 342 determines that the ROI pointer p1 and the first ROI r1 are overlapped with each other at Step S33 of FIG. 10 (Step S33: Yes), the distance determining unit 342 determines whether the ROI pointer p1 and the second ROI r2 are overlapped with each other (Step S46).

When the distance determining unit 342 determines that the ROI pointer p1 and the second ROI r2 are not overlapped with each other (Step S46: No), the display controller 32 switches the indicator of the first ROI r1 to the indicator in the selected state and causes the display 4 to display the ultrasound image 41 having the pointer marker p2 superimposed thereon (Step S47).

Figure 13:
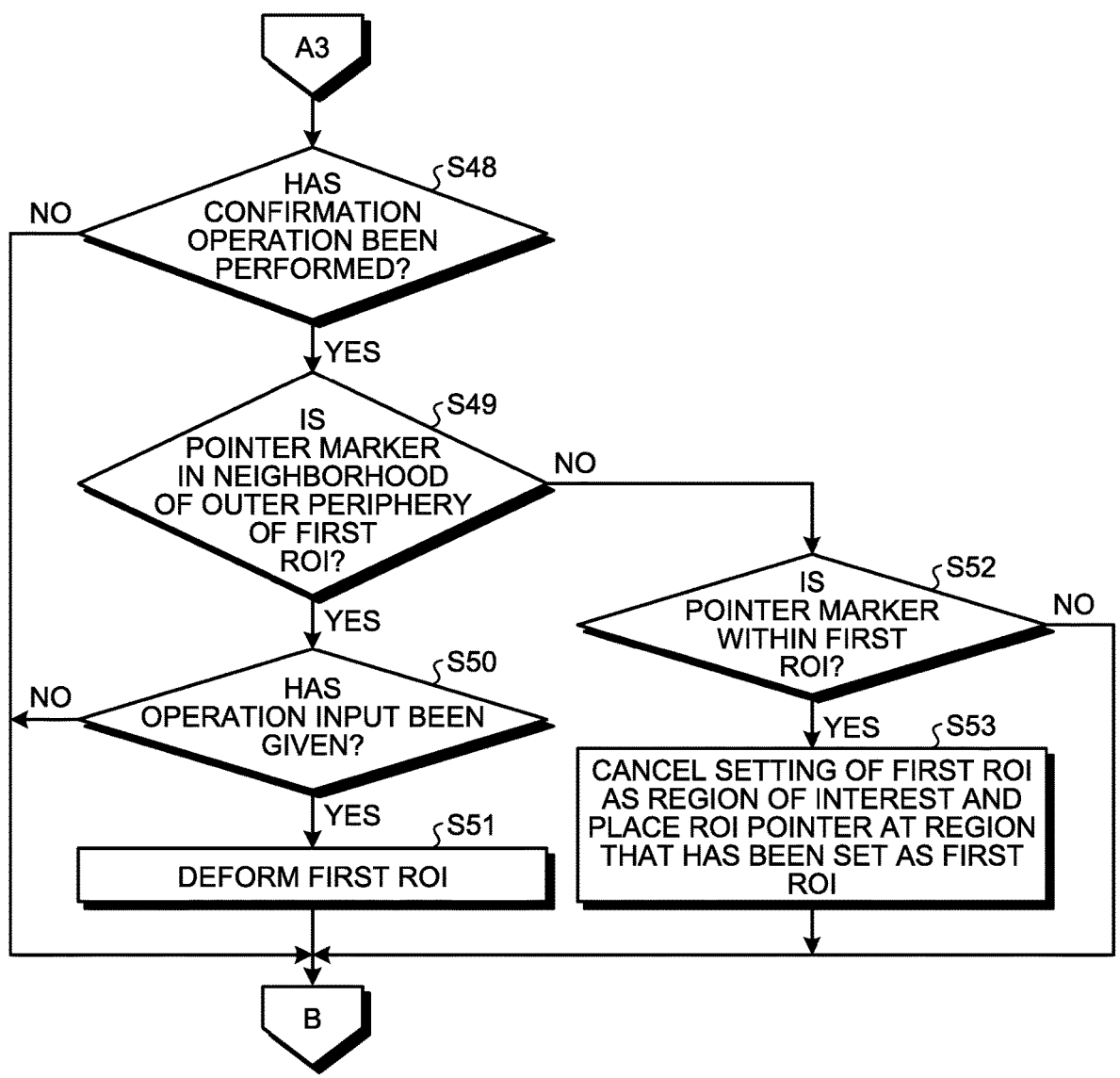
FIG. 13 is a flowchart that illustrates an operation in the ultrasound diagnosis system illustrated in FIG. 1 when two ROIs are set.

Then, the process transitions from A3 to FIG. 13, and the control unit 34 determines whether a confirmation operation has been performed (Step S48). When the control unit 34 determines that a confirmation operation has been performed (Step S48: Yes), the distance determining unit 342 determines whether the center position of the pointer marker p2 is in the neighborhood of the outer periphery of the first ROI r1 (Step S49).

When the distance determining unit 342 determines that the center position of the pointer marker p2 is in the neighborhood of the outer periphery of the first ROI r1 (Step S49: Yes), the control unit 34 determines whether an operation input has been given (Step S50).

Figure 20:
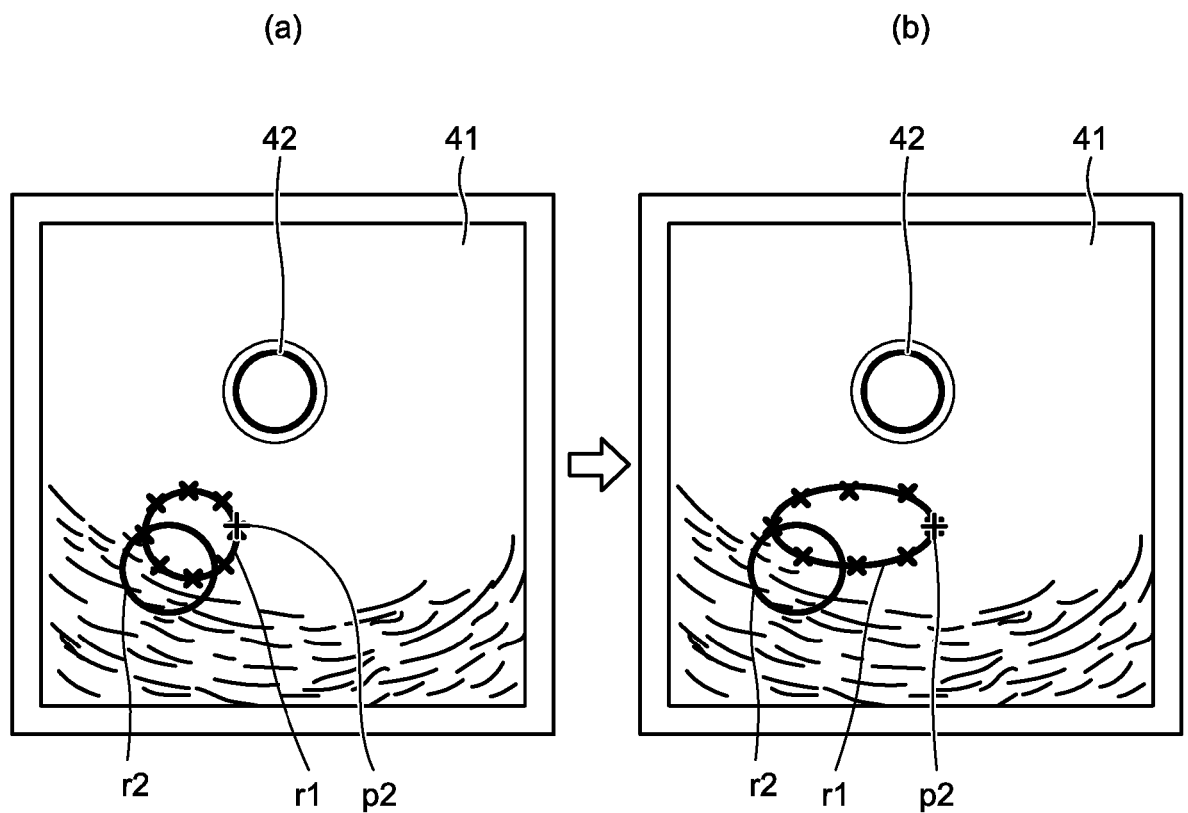
FIG. 20 is a diagram that illustrates the image displayed on the display when the first ROI is deformed.

When the control unit 34 determines that an operation input has been given (Step S50: Yes), the display controller 32 deforms the first ROI r1 in accordance with a movement of the input position corresponding to the operation input (Step S51). FIG. 20 is a diagram that illustrates the image displayed on the display when the first ROI is deformed. When the center position of the pointer marker p2 is located in the neighborhood of the outer periphery of the first ROI r1 in the selected state and when a confirmation operation is input, as illustrated in (a) of FIG. 20, the first ROI r1 is deformed in accordance with a movement of the input position, as illustrated in (b) of FIG. 20. Therefore, the first ROI r1 may be deformed without inconvenience. Then, the process returns to FIG. 10 from B so that a termination determination is made at Step S38, and the process is terminated or continued.

When the distance determining unit 342 determines that the center position of the pointer marker p2 is not in the neighborhood of the outer periphery of the first ROI r1 at Step S49 of FIG. 13 (Step S49: No), the distance determining unit 342 determines whether the center position of the pointer marker p2 is within the first ROI r1 (Step S52).

Figure 21:
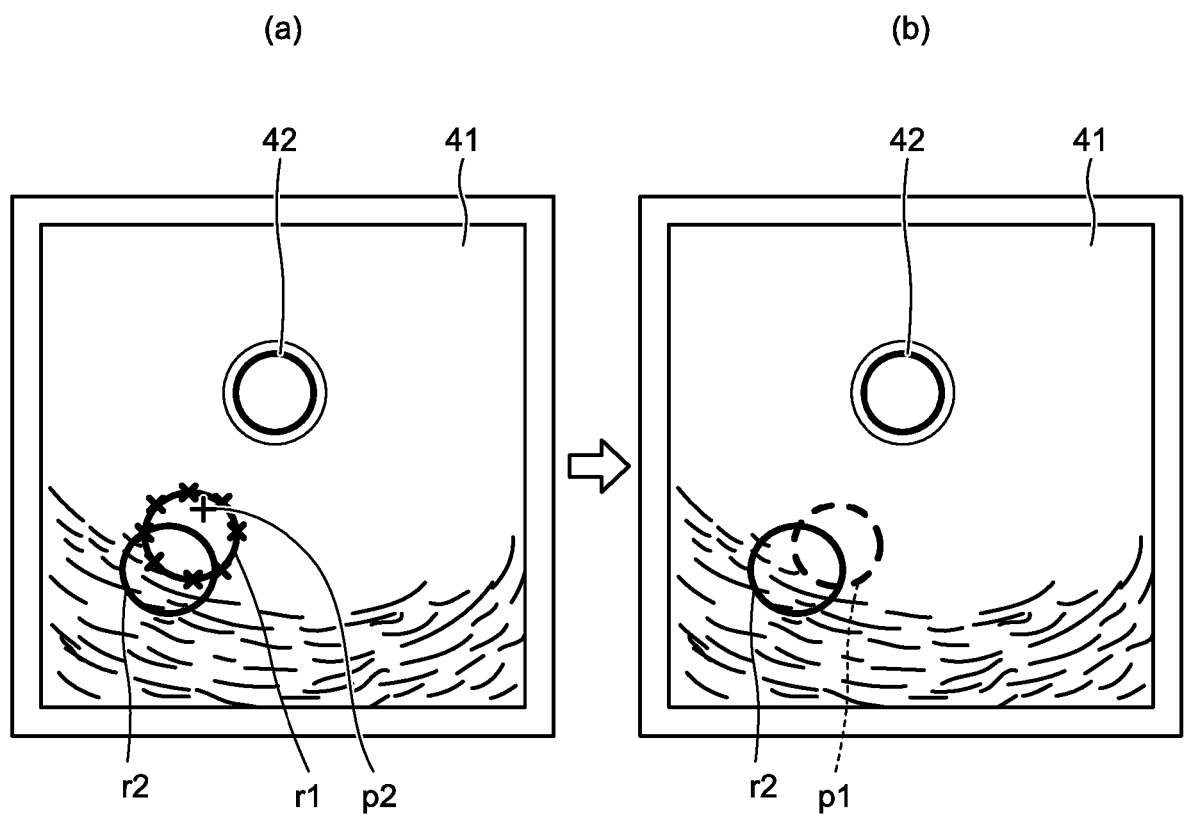
FIG. 21 is a diagram that illustrates the image displayed on the display when the setting of the first ROI as the region of interest is canceled.

When the distance determining unit 342 determines that the center position of the pointer marker p2 is within the first ROI r1 (Step S52: Yes), the region-of-interest setting unit 341 cancels the setting of the first ROI r1 as the ROI, and the display controller 32 places the ROI pointer p1 at the region that has been set as the first ROI r1 (Step S53). FIG. 21 is a diagram that illustrates the image displayed on the display when the setting of the first ROI as the region of interest is canceled. When the center position of the pointer marker p2 is located within the first ROI r1 and when a confirmation operation is input, as illustrated in (a) of FIG. 21, the indicator representing the first ROI r1 is deleted, and the ROI pointer p1 is displayed at the region that has been set as the first ROI r1, as illustrated in (b) of FIG. 21. By moving the ROI pointer p1 from this state, the first ROI r1 may be set again at any position. In other words, the first ROI r1 may be moved without inconvenience. Furthermore, in this state, by moving the ROI pointer p1 out of the ultrasound image 41, the set first ROI r1 may be deleted. Then, the process returns to FIG. 10 from B so that a termination determination is made at Step S38, and the process is terminated or continued.

At Step S52 of FIG. 13, when the distance determining unit 342 determines that the center position of the pointer marker p2 is not within the first ROI r1 (Step S52: No), the process returns to FIG. 10 from B so that a termination determination is made at Step S38, and the process is terminated or continued.

When the distance determining unit 342 determines that the ROI pointer p1 and the second ROI r2 are overlapped with each other at Step S46 of FIG. 10 (Step S46: Yes), the distance determining unit 342 determines whether the first ROI r1 and the second ROI r2 have an inclusion relation (Step S54).

When the distance determining unit 342 determines that the first ROI r1 and the second ROI r2 do not have an inclusion relation (Step S54: No), the display controller 32 sets the previously set ROI to the selected state and causes the pointer marker p2 to be displayed on the ultrasound image 41 (Step S55).

Figure 14:
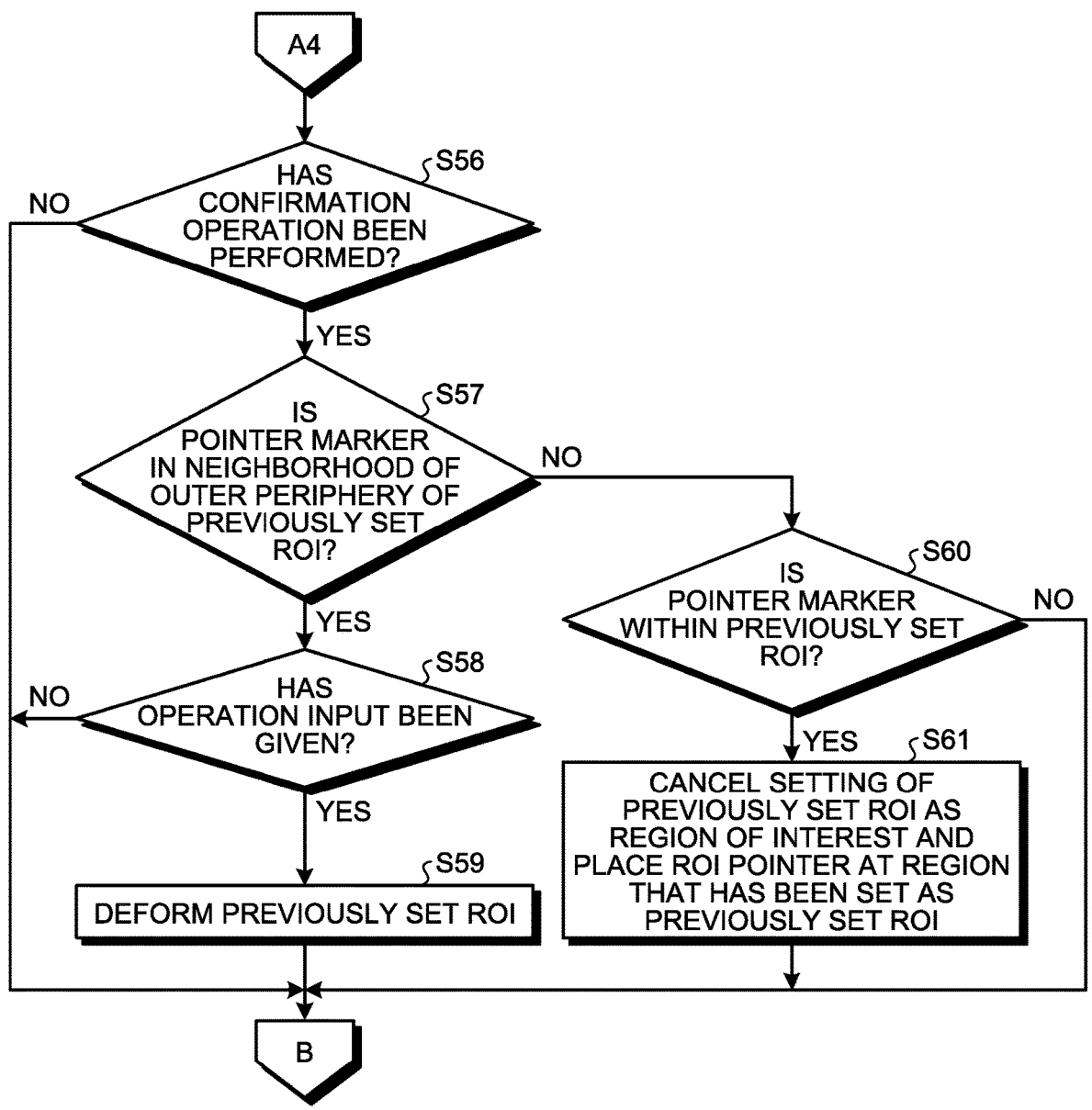
FIG. 14 is a flowchart that illustrates an operation in the ultrasound diagnosis system illustrated in FIG. 1 when two ROIs are set.

Then, the process transitions to FIG. 14 from A4, and the control unit 34 determines whether a confirmation operation has been performed (Step S56). When the control unit 34 determines that a confirmation operation has been performed (Step S56: Yes), the distance determining unit 342 determines whether the center position of the pointer marker p2 is in the neighborhood of the outer periphery of the previously set ROI (Step S57).

When the distance determining unit 342 determines that the center position of the pointer marker p2 is in the neighborhood of the outer periphery of the previously set ROI (Step S57: Yes), the control unit 34 determines whether an operation input has been given (Step S58).

Figure 22:
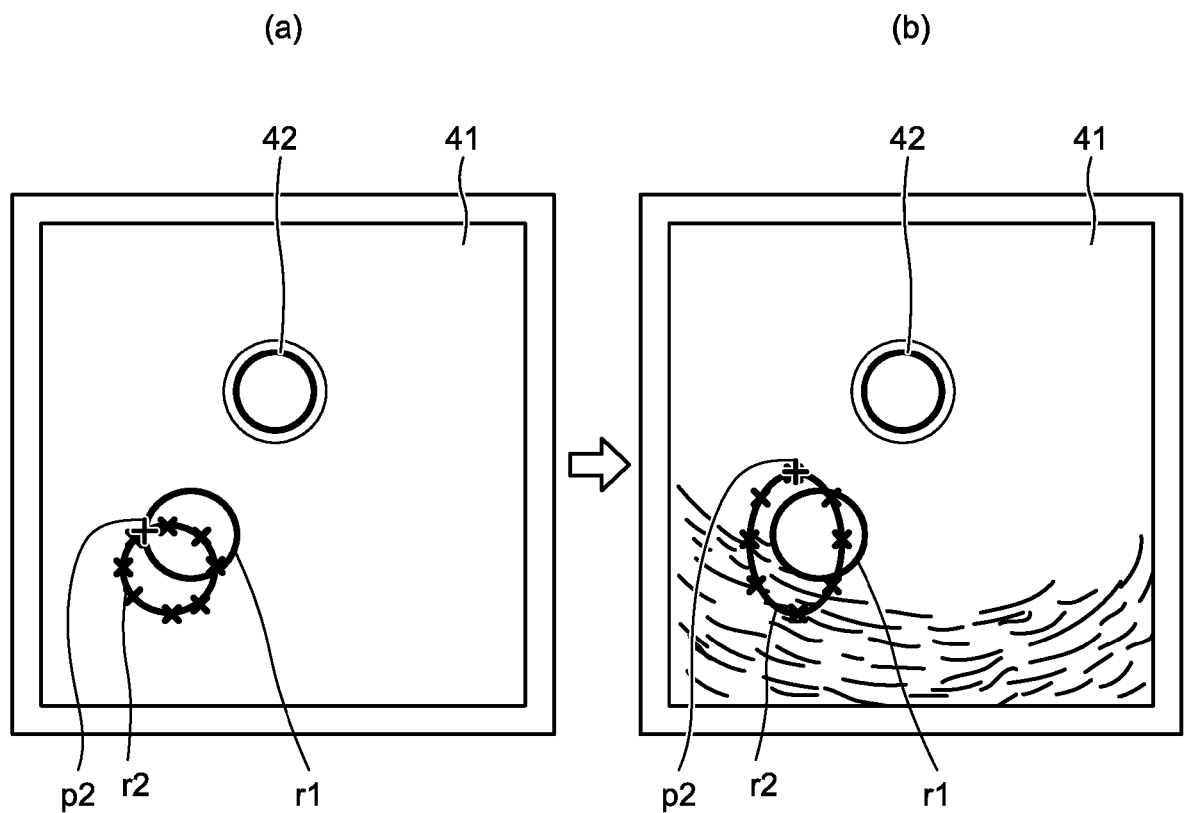
FIG. 22 is a diagram that illustrates the image displayed on the display when the previously set ROI is deformed in a case where the first ROI and the second ROI are overlapped with each other.

When the control unit 34 determines that an operation input has been given (Step S58: Yes), the display controller 32 deforms the previously set ROI in accordance with a movement of the input position corresponding to the operation input (Step S59). FIG. 22 is a diagram that illustrates the image displayed on the display when the previously set ROI is deformed in a case where the first ROI and the second ROI are overlapped with each other. In FIG. 22, the second ROI r2 is the previously set ROI. When the center position of the pointer marker p2 is located in the neighborhood of the outer periphery of the second ROI r2 in the selected state and when a confirmation operation is input, as illustrated in (a) of FIG. 22, the second ROI r2 is deformed in accordance with a movement of the input position, as illustrated in (b) of FIG. 22. Therefore, the previously set ROI may be deformed without inconvenience. Then, the process returns to FIG. 10 from B so that a termination determination is made at Step S38, and the process is terminated or continued.

When the distance determining unit 342 determines that the center position of the pointer marker p2 is not in the neighborhood of the outer periphery of the previously set ROI at Step S57 of FIG. 14 (Step S57: No), the distance determining unit 342 determines whether the center position of the pointer marker p2 is within the previously set ROI (Step S60).

Figure 23:
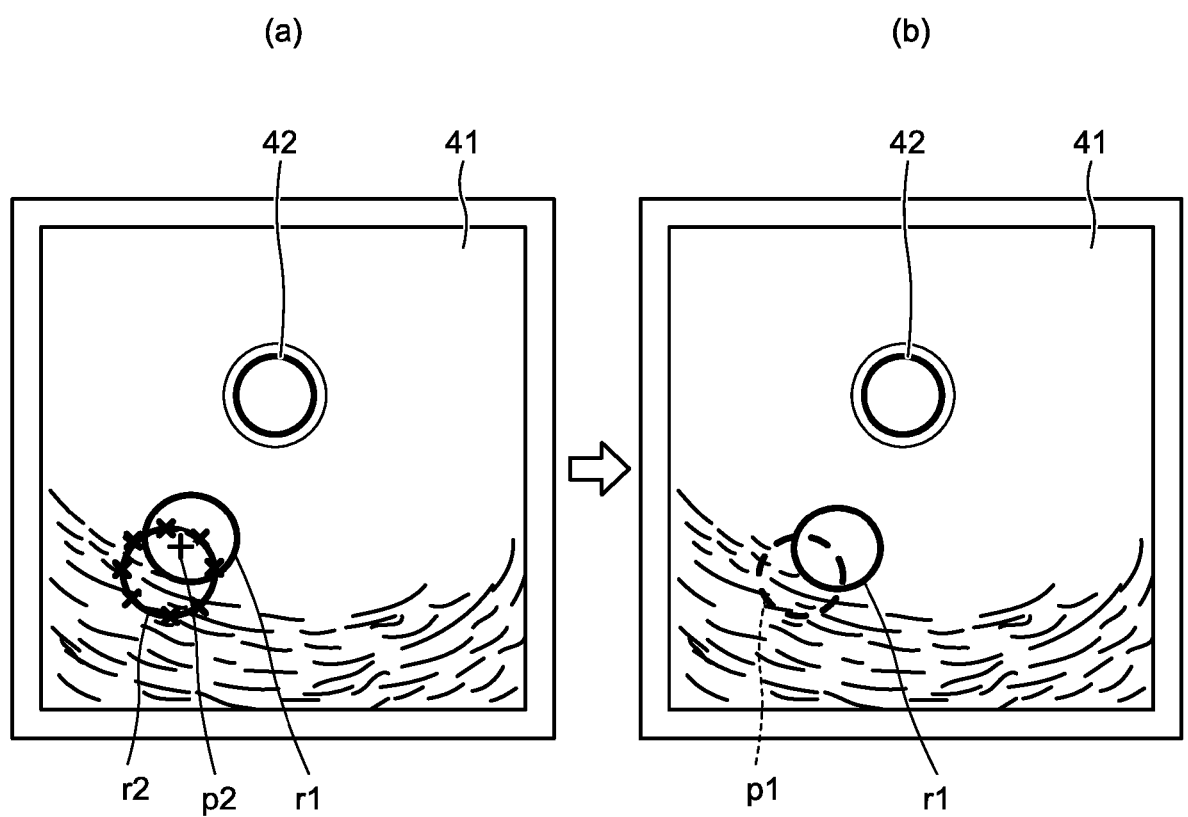
FIG. 23 is a diagram that illustrates the image displayed on the display when the setting of the previously set ROI is canceled in a case where the first ROI and the second ROI are overlapped with each other.

When the distance determining unit 342 determines that the center position of the pointer marker p2 is within the previously set ROI (Step S60: Yes), the region-of-interest setting unit 341 cancels the setting of the previously set ROI as the ROI, and the display controller 32 places the ROI pointer p1 in the region that has been set as the previously set ROI (Step S61). FIG. 23 is a diagram that illustrates the image displayed on the display when the setting of the previously set ROI is canceled in a case where the first ROI and the second ROI are overlapped with each other. In FIG. 23, the second ROI r2 is the previously set ROI. When the center position of the pointer marker p2 is located within the second ROI r2 and a confirmation operation is input, as illustrated in (a) of FIG. 23, the indicator representing the second ROI r2 is deleted and the ROI pointer p1 is displayed at the region that has been set as the second ROI r2, as illustrated in (b) of FIG. 23. By moving the ROI pointer p1 from this state, the previously set ROI may be set again at any position. In other words, the previously set ROI may be moved without inconvenience. Furthermore, in this state, by moving the ROI pointer p1 out of the ultrasound image 41, the previously set ROI may be deleted. Then, the process returns to FIG. 10 from B so that a termination determination is made at Step S38, and the process is terminated or continued.

When the distance determining unit 342 determines that the center position of the pointer marker p2 is not within the previously set ROI at Step S60 of FIG. 14 (Step S60: No), the process returns to FIG. 10 from B so that a termination determination is made at Step S38, and the process is terminated or continued.

When the distance determining unit 342 determines that the first ROI r1 and the second ROI r2 have an inclusion relation at Step S54 of FIG. 10 (Step S54: Yes), the display controller 32 causes the included ROI to enter the selected state and causes the pointer marker p2 to be displayed on the ultrasound image 41 (Step S62).

Figure 15:
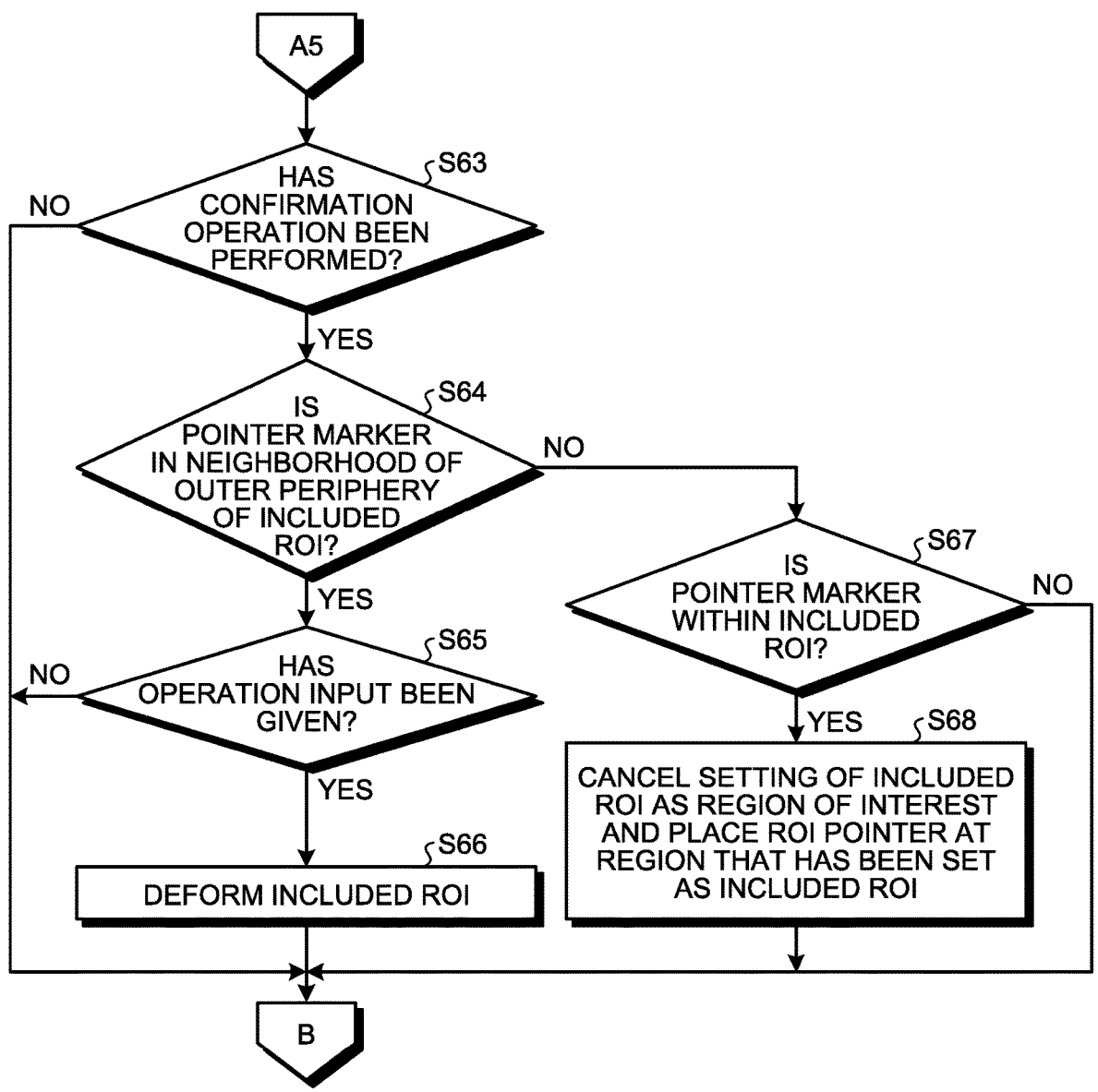
FIG. 15 is a flowchart that illustrates an operation in the ultrasound diagnosis system illustrated in FIG. 1 when two ROIs are set.

Then, the process transitions to FIG. 15 from A5, and the control unit 34 determines whether a confirmation operation has been performed (Step S63). When the control unit 34 determines that a confirmation operation has been performed (Step S63: Yes), the distance determining unit 342 determines whether the center position of the pointer marker p2 is in the neighborhood of the outer periphery of the included ROI (Step S64).

When the distance determining unit 342 determines that the center position of the pointer marker p2 is in the neighborhood of the outer periphery of the included ROI (Step S64: Yes), the control unit 34 determines whether an operation input has been given (Step S65).

Figure 24:
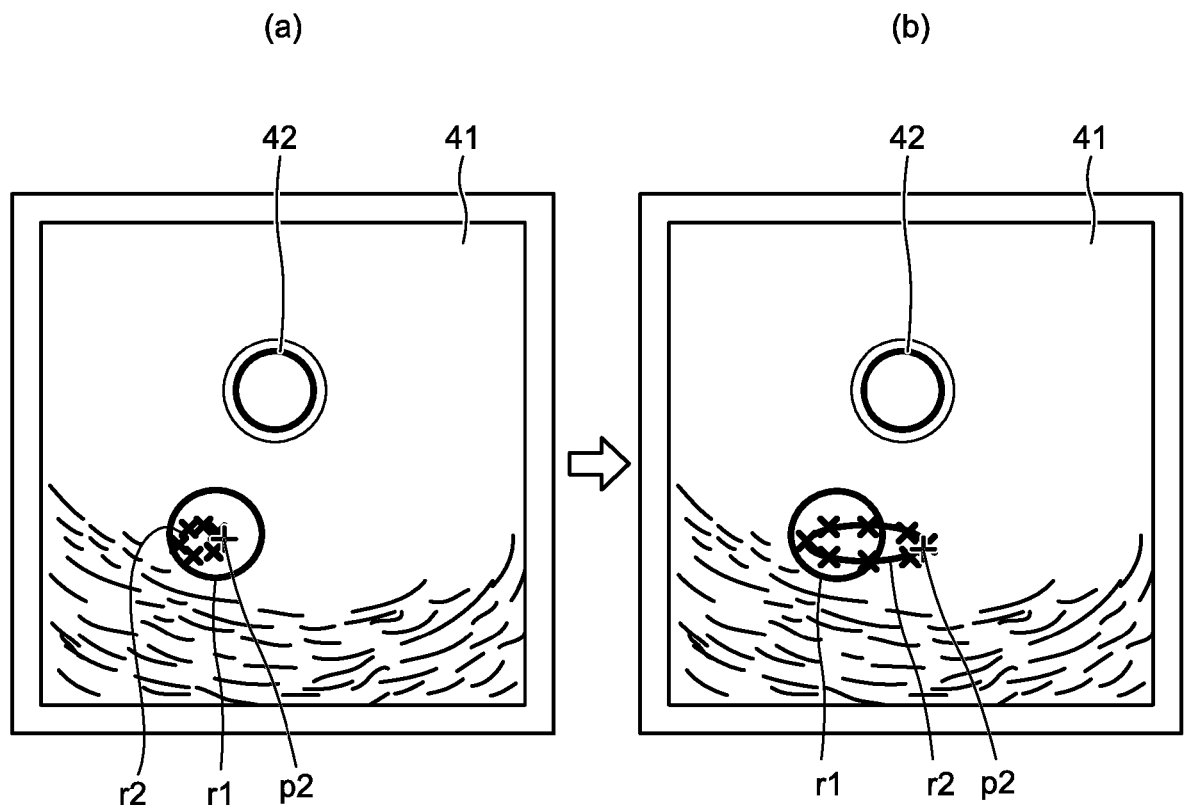
FIG. 24 is a diagram that illustrates the image displayed on the display when the included ROI is deformed in a case where the first ROI and the second ROI have an inclusion relation.

When the control unit 34 determines that an operation input has been given (Step S65: Yes), the display controller 32 deforms the included ROI in accordance with a movement of the input position corresponding to the operation input (Step S66). FIG. 24 is a diagram that illustrates the image displayed on the display when the included ROI is deformed in a case where the first ROI and the second ROI have an inclusion relation. In FIG. 24, the second ROI r2 is the included ROI. When the center position of the pointer marker p2 is located in the neighborhood of the outer periphery of the second ROI r2 in the selected state and when a confirmation operation is input, as illustrated in (a) of FIG. 24, the second ROI r2 is deformed in accordance with a movement of the input position, as illustrated in (b) of FIG. 24. Therefore, the included ROI may be deformed without inconvenience. Then, the process returns to FIG. 10 from B so that a termination determination is made at Step S38, and the process is terminated or continued.

When the distance determining unit 342 determines that the center position of the pointer marker p2 is not in the neighborhood of the outer periphery of the included ROI at Step S64 of FIG. 15 (Step S64: No), the distance determining unit 342 determines whether the center position of the pointer marker p2 is located within the included ROI (Step S67).

Figure 25:
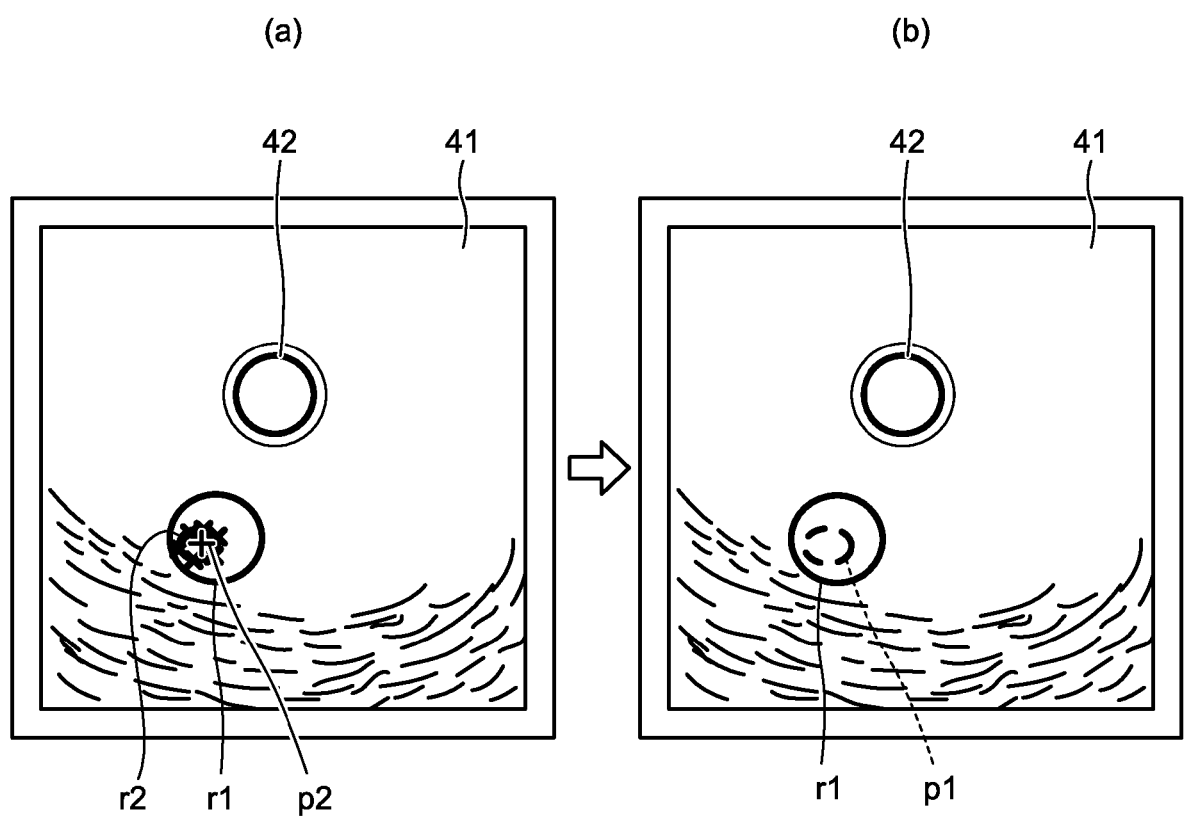
FIG. 25 is a diagram that illustrates the image displayed on the display when the setting of the included ROI is canceled in a case where the first ROI and the second ROI have an inclusion relation.

When the distance determining unit 342 determines that the center position of the pointer marker p2 is located within the included ROI (Step S67: Yes), the region-of-interest setting unit 341 cancels the setting of the included ROI as the ROI, and the display controller 32 places the ROI pointer p1 at the region that has been set as the included ROI (Step S68). FIG. 25 is a diagram that illustrates the image displayed on the display when the setting of the included ROI is canceled in a case where the first ROI and the second ROI have an inclusion relation. In FIG. 25, the second ROI r2 is an included ROI. When the center position of the pointer marker p2 is located within the second ROI r2 and when a confirmation operation is input, as illustrated in (a) of FIG. 25, the indicator representing the second ROI r2 is deleted, and the ROI pointer p1 is displayed at the region that has been set as the second ROI r2, as illustrated in (b) of FIG. 25. By moving the ROI pointer p1 from this state, the included ROI may be set again at any position. In other words, the included ROI may be moved without inconvenience.

Furthermore, in this state, by moving the ROI pointer p1 out of the ultrasound image 41, the included ROI may be deleted. Then, the process returns to FIG. 10 from B so that a termination determination is made at Step S38, and the process is terminated or continued.

When the distance determining unit 342 determines that the center position of the pointer marker p2 is not located within the included ROI at Step S67 of FIG. 15 (Step S67: No), the process returns to FIG. 10 from B so that a termination determination is made at Step S38, and the process is terminated or continued.

When the control unit 34 determines that there are multiple input positions input from the input device 5 at Step S32 of FIG. 10 (Step S32: Yes), the display controller 32 causes the display 4 to display the ultrasound image 41 constantly having the ROI pointer p1 superimposed thereon at the position corresponding to the operation input on the ultrasound image 41 (Step S69).

Figure 16:
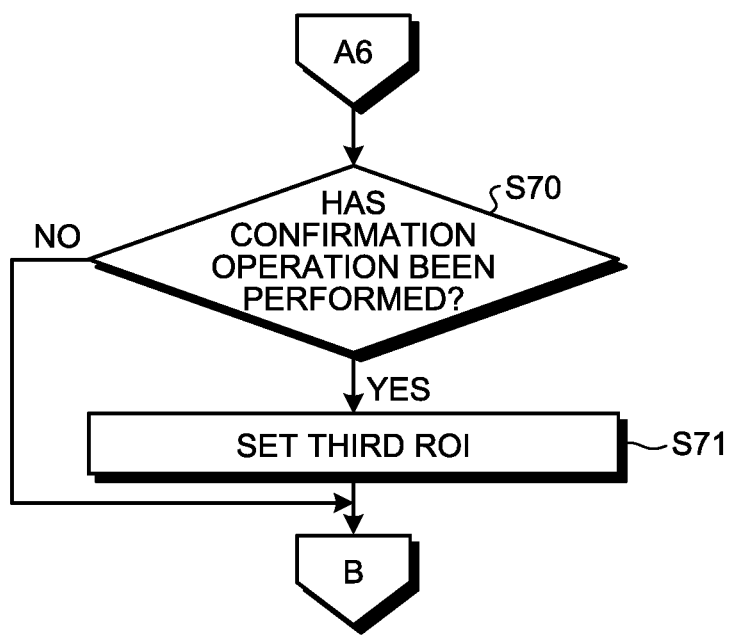
FIG. 16 is a flowchart that illustrates an operation in the ultrasound diagnosis system illustrated in FIG. 1 when two ROIs are set.
Figure 26:
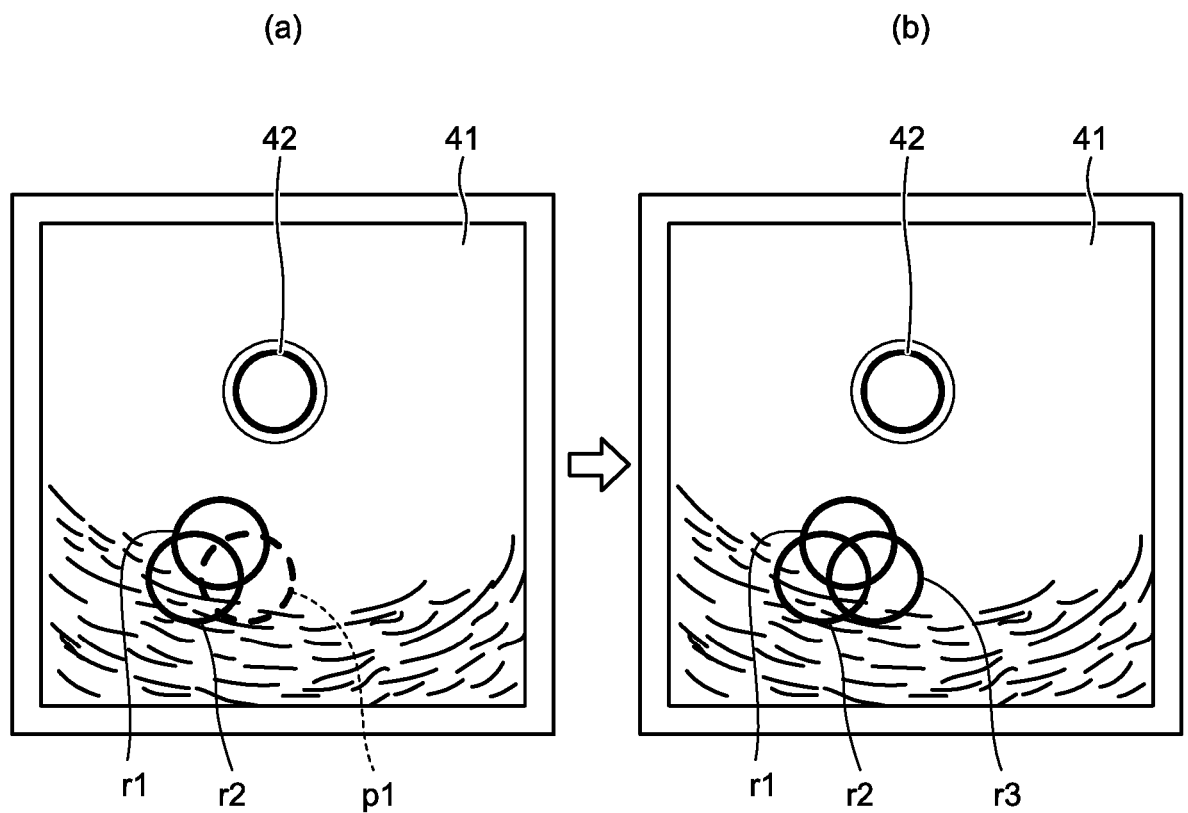
FIG. 26 is a diagram that illustrates the image displayed on the display when the third ROI is set in a case where the first ROI and the second ROI are overlapped with each other.

Then, the process transitions to FIG. 16 from A6, and the control unit 34 determines whether a confirmation operation has been performed (Step S70). When the control unit 34 determines that a confirmation operation has been performed (Step S70: Yes), the region-of-interest setting unit 341 sets the region corresponding to the ROI pointer p1 within the ultrasound image 41 as the region of interest (the third ROI r3) (Step S71). FIG. 26 is a diagram that illustrates the image displayed on the display when the third ROI is set in a case where the first ROI and the second ROI are overlapped with each other. In a case where the operator makes operation inputs with two or more fingers, when the ROI pointer p1 is moved from the position where the ROI pointer p1 and the first ROI r1 or the second ROI r2 are not overlapped with each other to the position ((a) of FIG. 26) where the ROI pointer p1 and the first ROI r1 or the second ROI r2 are overlapped with each other, the display controller 32 causes the display 4 to continuously display the ultrasound image 41 having the ROI pointer p1 superimposed thereon. Then, when a confirmation operation is performed in a state where the ROI pointer p1 and the first ROI r1 or the second ROI r2 are overlapped with each other, the region-of-interest setting unit 341 sets the region corresponding to the ROI pointer p1 within the ultrasound image 41 as the region of interest (the third ROI r3), as illustrated in (b) of FIG. 26. In other words, the region overlapped with the first ROI r1 or the second ROI r2 may be set as the region of interest (the third ROI r3) without inconvenience by the operator performing an operation with two fingers. Then, the process returns to FIG. 10 from B so that a termination determination is made at Step S38, and the process is terminated or continued.

Furthermore, when an operation is not performed for more than a predetermined time period at the step (Steps S31, S42, S50, S58, S65) for determining whether an operation input has been given and the step (Step S36, S40, S48, S56, S63, S70) for determining whether a confirmation operation has been performed, the process returns to FIG. 10 from B so that a termination determination is made at Step S38, and the sequence of processes is terminated or continued.

Furthermore, in a case where three or more ROIs are set, it is determined whether the ROIs are overlapped with each other or the ROIs have an inclusion relation in the same manner as in the case where there are two ROIs, whereby the same process may be performed.

As described above, with the ultrasound diagnosis system 1, an indicator superimposed on the ultrasound image 41 and the control responsive to an operation input are switched in accordance with the positional relationship between the ROI pointer p1 or the pointer marker p2 and the set ROI, whereby it is possible to switch the operation for setting a new region of interest and the operation for editing the already set region of interest without inconvenience.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor comprising hardware, wherein the processor is configured to:
    cause a display to display an image having a first pointer superimposed thereon, the first pointer having a predetermined shape;
    move a position of the first pointer within the image in accordance with an input position that is input from an input device;
    in response to a first confirmation operation for confirming the input position being input to the input device, set a region corresponding to the position of the first pointer within the image as one region of interest
    determine whether a distance between a first representative position of the first pointer and a second representative position of another region of interest, the first representative position of the first pointer being a position according to the input position that is input to the input device after the one region of interest is set, is shorter than a predetermined distance; and
    in response to determining that the distance between the first representative position and the second representative position is shorter than the predetermined distance:
        switch a first indicator of the another region of interest to a second indicator in a selected state notifying that the another region of interest is being selected;
        switch the first pointer to a second pointer different from the first pointer; and
        cause the display to display the image having the second indicator and the second pointer superimposed on the image.

2. The image processing apparatus according to claim 1, wherein the processor is configured to:
    in response to a second confirmation operation being input to the input device:
        determine whether a shortest distance between a center position of the second pointer and an outer periphery of the another region of interest is shorter than a second predetermined distance; and
        in response to determining that the shortest distance between the center position of the second pointer and the outer periphery of the another region of interest is shorter than the second predetermined distance, deform the another region of interest in accordance with a movement of the input position that is input.

3. The image processing apparatus according to claim 2, wherein the processor is configured to:
    in response to determining that the shortest distance between the center position of the second pointer and the outer periphery of the another region of interest is not shorter than the second predetermined distance:
        determine whether the center position of the second pointer is within the another region of interest; and
        in response to determining that the center position of the second pointer is within the another region of interest:
            cancel a setting of the another region of interest; and
            place the first pointer in a region of which the setting as the another region of interest has been cancelled.

4. The image processing apparatus according to claim 1, wherein the processor is configured to:
    determine whether the region corresponding to the position of the first pointer is overlapped with the another region of interest; and
    in response to determining that the region corresponding to the position of the first pointer is overlapped with the another region of interest, switch a first indicator of the region corresponding to the position of the first pointer overlapped with the another region of interest to a second indicator in a selected state notifying that the region corresponding to the position of the first pointer is the one region of interest.

5. The image processing apparatus according to claim 1, wherein the processor is configured to:
    determine whether the another region of interest has an inclusion relation with at least any one of regions of interest other than the one region of interest; and
    in response to determining that the distance between the first representative position and the second representative position is shorter than the predetermined distance and determining that the another region of interest has the inclusion relation with the at least any one of regions of interest other than the one region of interest
        switch a first indicator of the at least any one of regions of interest having the inclusion relation with the another region of interest to a second indicator in a selected state notifying that the at least any one of regions of interest is being selected; and
        cause the display to display the image having the second indicator notifying that the another region of interest is being selected, the second indicator notifying that the at least any one of regions of interest having the inclusion relation with the another region of interest is selected and the second pointer superimposed on the image.

6. The image processing apparatus according to claim 1, wherein the processor is configured to, in response to two or more inputs of the input position that is input from the input device, cause the display to display the image constantly having the first pointer superimposed thereon.

7. The image processing apparatus according to claim 1, wherein the image is an ultrasound image generated based on an ultrasound signal received from an ultrasound transducer configured to transmit an ultrasound wave to an observation target and receive an ultrasound wave reflected by the observation target.

8. An ultrasound diagnosis system comprising:
the image processing apparatus according to claim 1; and
an ultrasound endoscope comprising an ultrasound transducer configured to transmit an ultrasound wave to an observation target, receive an ultrasound signal reflected by the observation target, and output the ultrasound signal to the image processing apparatus, wherein the processor of the image processing apparatus is configured to process the ultrasound signal to generate the image.

9. An operation method of an image processing apparatus, the operation method comprising:
   causing a display to display an image having a first pointer superimposed thereon, the first pointer having a predetermined shape;
   moving a position of the first pointer within the image in accordance with an input position that is input from an input device;
   in response to a first confirmation operation for confirming the input position being input to the input device, setting a region corresponding to the position of the first pointer within the image as one region of interest;
   determining whether a distance between a first representative position of the first pointer and a second representative position of another region of interest, the first representative position of the first pointer being a position according to the input position that is input to the input device after the one region of interest is set, is shorter than a predetermined distance; and
   in response to determining that the distance between the first representative position and the second representative position is shorter than the predetermined distance:
      switching a first indicator of the another region of interest to a second indicator in a selected state notifying that the another region of interest is being selected;
      switching the first pointer to a second pointer different from the first pointer; and
      causing the display to display the image having the second indicator and the second pointer superimposed on the image.

10. A non-transitory computer-readable recording medium having an executable program recorded therein, the executable program instructing a processor to execute the following:
   causing a display to display an image having a first pointer superimposed thereon, the first pointer having a predetermined shape;
   moving a position of the first pointer within the image in accordance with an input position that is input from an input device;
   in response to a first confirmation operation for confirming the input position being input to the input device, setting a region corresponding to the position of the first pointer within the image as one region of interest;
   determining whether a distance between a first representative position of the first pointer and a second representative position of another region of interest, the first representative position of the first pointer being a position according to the input position that is input to the input device after the one region of interest is set, is shorter than a predetermined distance; and
   in response to determining that the distance between the first representative position and the second representative position is shorter than the predetermined distance:
      switching a first indicator of the another region of interest to a second indicator in a selected state notifying that the another region of interest is being selected;
      switching the first pointer to a second pointer different from the first pointer; and
      causing the display to display the image having the second indicator and the second pointer superimposed on the image.

* * * * *